(12) United States Patent
Claps

(10) Patent No.: US 7,944,555 B2
(45) Date of Patent: May 17, 2011

(54) HIGH-SPEED, RUGGED, TIME-RESOLVED, RAMAN SPECTROMETER FOR SENSING MULTIPLE COMPONENTS OF A SAMPLE AND FOR DIAGNOSTICS OF PATHOLOGICAL SKIN CONDITIONS SUCH AS CANCER

(75) Inventor: Ricardo Claps, San Jose, CA (US)

(73) Assignee: Optical Oncology, Inc., Somerset, NJ (US)

( * ) Notice: Subject to any disclaimer, the term of this patent is extended or adjusted under 35 U.S.C. 154(b) by 0 days.

(21) Appl. No.: 12/551,404

(22) Filed: Aug. 31, 2009

(65) Prior Publication Data

US 2010/0027002 A1 Feb. 4, 2010

Related U.S. Application Data

(63) Continuation-in-part of application No. 11/452,129, filed on Jun. 12, 2006, now Pat. No. 7,602,488.

(51) Int. Cl.
*G01J 3/44* (2006.01)
(52) U.S. Cl. .................................................. 356/301
(58) Field of Classification Search .................... 356/301
See application file for complete search history.

(56) References Cited

U.S. PATENT DOCUMENTS

| 5,243,983 | A | | 9/1993 | Tarr et al. |
| 5,261,410 | A | | 11/1993 | Alfano et al. |
| 6,151,522 | A | * | 11/2000 | Alfano et al. .................. 356/301 |
| 2003/0166436 | A1 | * | 9/2003 | Gramaccioni .................. 482/57 |
| 2005/0162646 | A1 | * | 7/2005 | Tedesco et al. ................ 356/301 |
| 2007/0285658 | A1 | | 12/2007 | Claps et al. |
| 2008/0319712 | A1 | | 12/2008 | Claps |

OTHER PUBLICATIONS

American Cancer Society, "Cancer Fact & Figures, 2007". http://www.cancer.org/downloads/STT/CAFF2007PWSecured.pdf, 2007.
"What you need to know about skin cancer," National Cancer Institute: http://www.cancer.gov/.
"What you need to know about skin melanoma," National Cancer Institute: http://www.cancer.gov/.
M. C. Stoppler; "Skin Biopsy", http://www.medicinenet.com/skin_biopsy/article.htm.
Yale Department of Genetics: Molecular Cytogenetics services: http://info.med.yale.edu/genetics/cytogenetics/cytogenetics_testInfo.php.
D. C. Fernandez, R. Bhargava, S.M. Hewitt, I.W. Levin; "Infrared spectroscopic imaging for histopathologic recognition", Nature Biotechnology, 23(4) 469 (2005).
V. McGovern; "Digital Diagnosis: New Tool for Detecting Skin Cancer", Environmental Health Perspectives 111(14) A770 (2003).
Ediscim project: http://www.ediscim.com/ (2004); Project funded by the European Community with the collaboration of VisiTech International http://www.visitech.co.uk/.
Samba technologies (acquired by Tribvn Medical, France http://www.tribvn.com/tribvn/ent/histpage_us.htm.

(Continued)

*Primary Examiner* — Kara E Geisel
(74) *Attorney, Agent, or Firm* — Greenberg Traurig, LLP

(57) ABSTRACT

A new architecture for implementing a time-resolved Raman spectrometer is 2-3 orders of magnitude faster than current systems. In one embodiment, the invention employs a rotating optical switch to time multiplex an input signal through multiple band-pass filters and into a single optical detector which is electrically activated only when the filtered input light pulse is about to impact it.

Time-multiplexing the input signal through multiple optical filters and time-sequencing the optical detector enables the device to detect and analyze 2-3 orders of magnitude faster than current designs. In one embodiment, the system may be employed for the diagnostics of a pathological condition of skin tissue in patients, such as malignant melanoma or other types of skin cancers and abnormal conditions.

26 Claims, 22 Drawing Sheets

OTHER PUBLICATIONS

M. Gniadecka, H.C. Wulf, N. N. Mortensen, O.F. Nielsen, D.H. Christensen; "Diagnosis of Basal Cell Carcinoma by Raman Spectroscopy", J. Raman Spectrosc. 28 125 (1997).

S. Sigurdsson, P.A. Philipsen, L.K. Hansen, J. Larsen, M. Gniadecka, H.C. Wulf; "Detection of Skin Cancer by Classification of Raman Spectra", IEEE Transactions on Biomedical Engineering, 51(10) 1784 (2004).

J. Choi, J. Choo, H. Chung, D-G Gweon, J. Park, H.J. Kim, S. Park, C-H Oh; "Direct Observation of Spectral Differences Between Normal and Basal Cell Carcinoma (BCC) Tissues Using Confocal Raman Microscopy", Biopolymers, 77, 264 (2005).

M. Gniadecka, P.A. Philipsen, S. Sigurdsson, S. Wessel, O.F. Nielsen, D. H. Christensen, J. Hercogova, K. Rossen, H.K. Thomsen, R. Gniadecki, L.K. Hansen, H.C. Wulf; "Melanoma diagnosis by Raman Spectroscopy and Neural Networks: Structure Alterations in Proteins and Lipids in Intact Cancer Tissue", The Journal of Investigative Dermatology 122 443 (2004).

M. D. Keller, E.M. Kanter, A. Mahadevan-Jansen; "Raman Spectroscopy for Cancer Diagnosis", Spectroscopy 21(11) 33 (2006).

R. Bitar, M. Moreno, A. Oliveira, S. Cartaxo, H. Martinho, A.M. do Espirito Santo, I.D. Santos, L. M. Ferreira, A. Martin; "Raman Spectra of Pigmented Skin Conditions" Proc. SPIE vol. 6430, 64301E (2007).

Z. Huang, H. Lui, X.K. Chen, A. Alajlan, D.I. McLean, H. Zeng; "Raman spectroscopy of in vivo cutaneous melanin", J. Biomed. Opt. 9(6) 1198 (2004).

R. Claps, R. Guynn, W. Serafin, J. Virojanapa, A. Urbas, R.A. Lodder; "Real-time, broad-band measurement of cholesterol, collagen and elastin using a Novel Rotary Switch Spectrometer", Proceedings, SPIE vol. 6078, 60782G (2006).

N. Stone et al., "Near-infrared Raman spectroscopy for the classification of epithelial pre-cancers and cancers," Journal of Raman Spectroscopy, pp. 564-573, 2002.

Z. Huang et al., "Raman Spectroscopy in Combination with Background Near-Infrared Autofluoresence Enhances the In Vivo Assessment of Malignant Tissues," Photochemistry and Photobiology, pp. 1219-1226, (2005).

R.R. Alfano, "A New Weak Light Detection Technique: Reduction of Scattered Light and Ghosts in a Raman Spectrum by a Frequency Discriminating Optical Chopper," Applied Optics, vol. 8, No. 10, (Oct. 1969).

C.H. Liu et al., "Raman, fluorescence, and time-resolved light scattering as optical diagnostic techniques to seprate diseased and normal biomedical media," J. Photochem. Photobiol, pp. 187-209, (1992).

H. Talbot et al., "An overview of the Polartechnics SolarScan melanoma diagnosis algorithms," CSIRO, Mathematical and Information Sciences, {Hughues.Talbot,Leanne.Bischof}@csiro.au.

C.A. Lieber et al., "Handheld confocal Raman microspectrometer for in-vivo skin cancer measurement," Biomedical Vibrational Spectroscopy/Biohazard Detection Technologies, vol. 5321, (2004).

* cited by examiner

HIGH-SPEED, RUGGED, TIME-RESOLVED, RAMAN SPECTROMETER FOR SENSING MULTIPLE COMPONENTS OF A SAMPLE AND FOR DIAGNOSTICS OF PATHOLOGICAL SKIN CONDITIONS SUCH AS CANCER

CONTINUATION IN PART

The following disclosure is a continuation in part application of U.S. patent application Ser. No. 11/452,129 filed Jun. 12, 2006, now U.S. Pat. No. 7,602,488, incorporated herein by reference in its entirety.

PRIORITY

The following disclosure claims priority to co-pending U.S. patent application Ser. Nos. 11/603,939, and 11/767,458, incorporated herein by reference in their entirety.

FIELD OF THE INVENTION

This invention relates to a time-resolved Raman spectrometer that is two to three orders of magnitude faster than current Raman spectrometers and which is environmentally rugged, low cost and can detect multiple components of a sample simultaneously and which can be used to detect pathological conditions of skin tissue, such as cancer.

BACKGROUND OF THE INVENTION

Skin cancer is the most common type of cancer in the US. Approximately 1,000,000.0 Americans are diagnosed with it every year, with a death rate of ~2,000.0/year. According to the U.S. National Institute of Health, ultraviolet (UV) radiation from the sun is the main cause of skin cancer. Artificial sources can also cause skin cancer. The risk of developing skin cancer is also related to the place where the person lives. People who live in areas that receive high levels of UV radiation from the sun are more likely to develop skin cancer. In the United States, skin cancer is more common in Texas and Florida than it is in Minnesota or Wyoming. Worldwide, the places with highest rates of skin cancer are South Africa and Australia.

There are several types of tumor tissue in the skin that may or may not be able to spread to other tissues and pose a serious life threat (metastasis). There are mainly three malign tumor conditions of the skin: Malignant Melanoma (MM), Basal Cell Carcinoma (BCC), and Squamous Cell Carcinoma (SCC). MM can metastasize rapidly, it is diagnosed correctly with about 75% efficiency, by a trained dermatologist. Melanoma is the most serious form of skin cancer; about 60,000 people will be diagnosed with it in the US, this year (2009). BCC is the most common skin tumor, it does not metastasize. There is 65% correct diagnosis of BCC for practicing dermatologists. Some of the benign tumor tissues are known as Seborrhoeic Keratosis (SK) and Pigmented Nevi (NV). One of the important tasks of any diagnostics tool for skin cancer is to be able to discriminate between these five different tissue conditions.

The gold standard for detection and diagnosis of Melanoma is histopathology. This procedure is performed on a biopsy sample by a specialized dermatologist. Although it is highly subjective, it can be stated that on average, for malignant Melanoma, this procedure has an 80% sensitivity (percent of positive measurements, relative to sampling universe). The specificity of the technique (percent of true positives plus true negatives, relative to sampling universe) usually varies from 40% to 80%, depending on the level of expertise of the clinical staff. The overall efficacy of the technique, defined as the product, specificity×sensitivity is therefore well below 0.6 (60%). This procedure is highly invasive, time consuming, uncomfortable and costly. Added to the intrinsic cost of the procedure is the fact that between 95% to 98% of them result in negative diagnostics, meaning that the incurred cost was essentially unnecessary. The problem at hand therefore consists in the development of a diagnostics technique that is objective and repeatable, non-invasive, has low cost, and outperforms the dermatologist's sensitivity and specificity for the measurement. Furthermore, there is a solid potential for using this device in other types of cancerous malignancies in different tissues, or in a more sophisticated configuration, like a microscopic imaging device.

Raman spectroscopy is a proven technology in biomedical, chemical, industrial and other sensing applications. However, significant problems exist for implementing this technique, such as detector sensitivity, processing speed, simultaneous multi-component analysis of a single sample, environmental ruggedness, and cost. In order to obtain Raman spectra from a sample, a high intensity optical source is needed (typically a laser) to pump the inelastic Raman scattering process within the material, be it a gas, a liquid, or a solid. As a result, the material scatters radiation in all directions, at different frequencies. The component with frequency equal to that of the pump laser corresponds to Rayleigh scattering, and the component with frequency shifted lower than that of the pump laser is called Stokes radiation, a portion of which corresponds to Raman scattering. The main feature of Raman scattering is that it occurs regardless of the wavelength of the pumping optical source, while keeping the frequency shift between Stokes and pump radiation fixed. The Stokes radiation shift and intensity are dependent upon the material. Typically, Stokes Raman shifts are in the order of a few to tens of tera-Hertz (THz), and their intensity is 4 to 5 orders of magnitude lower than the Rayleigh scattered light. In order to discriminate and measure accurately the Raman scattered radiation from the Rayleigh radiation, a blocking filter for the Rayleigh frequency needs to be used in all Raman measurement systems. Fortunately, the typical Raman Stokes shift is large enough to allow for current state-of-the-art filters to block the Rayleigh radiation while marginally affecting the Raman Stokes radiation.

Time-resolved Raman spectroscopy techniques have been used for years. Detection and analysis of the signal in these systems is typically difficult and expensive. Commercial Raman spectrometers are:

1) too slow for many practical applications, with signal processing time of a few seconds or more. Real-time process monitoring is impossible, as are many medical and in-vivo applications;

2) typically limited to measuring no more than two or three components within a given sample, at a time, due to high spectral overlap between different analytes;

3) physically sensitive to the environment such as movement, vibration, and temperature changes, in their performance; and 4) not optically sensitive for many applications such as detecting weak markers in biological samples or weak returns and noisy signals from long-range sensing applications.

Techniques for processing multiple components, in the order of 20 to 100, with a 1 to 10 second typical collection for each, require an excessive amount of time to complete a full sample analysis. Weak signals from noisy environments result in the loss of important spectral information in many cases. Field applications in harsh environments are also off limits for currently available Raman systems.

The most popular types of spectrometers in use today are Fourier-Transform type devices. Fourier Transform Infra-red (FTIR) and Fourier Transform Raman (FTR) spectrometers employ a motor to create a linear displacement of sensitive optical elements in the detection process. This technique has serious operational and environmental limitations, since alignment must be maintained as optical parts are being moved, and also time-calibration is necessarily complex since non-uniform linear motion is involved.

Accordingly, there is a need for simple, environmentally insensitive Raman spectrometers capable of determining multiple components in a sample within a very short time. There is also a need for a reliable and simple mechanism for performing skin analysis that can adequately determine whether or not a biopsy needs to be collected from an individual in order to determine if certain portion of the skin is affected by a pathologic condition that requires immediate attention, like malignant melanoma.

SUMMARY

The embodiments described in the present disclosure provide an environmentally rugged system that performs high-speed Raman spectroscopy with dramatically improved processing speed, enabling the monitoring of multiple components of a sample in a very short time. One embodiment of the system includes the unique ability to process and analyze an individual material sample with a time resolution of 1 ms to 100 ms.

By using an ultra-sensitive photo-detector to enhance the system's sensitivity at high speed, the system provides the same sensitivity as current state-of-the-art devices Raman spectrometers but at a much higher speed. The system provides a simple time-calibration of the signal from the sample, therefore improving the accuracy of data collection at a reduced cost.

The system can quantitatively determine a mixture composed of multiple components (for example 20 to 25 or more components), simultaneously.

The system eliminates the use of gratings, prisms, and other dispersive elements that have large optical loss, are expensive, and extremely sensitive to alignment. The system uses a single photo-sensitive element, replacing the need for expensive photo-detector arrays and CCD cameras, and simplifying data collection schemes.

Some embodiments of the system provides a wide detection bandwidth, being able to detect signals with bandwidths from 900 nm to 2.1 µm.

An embodiment of the system uses a discrete version of Principal Component Analysis (dPCA) thereby reducing the number of data points to be processed by two orders of magnitude relative to state-of-the-art systems.

The system makes possible a method to perform time-resolved Raman analysis of blood vessel angiography and also makes possible a method for fast detection of calcified plaque in a blood vessel, for real-time diagnosis. Also the Raman spectroscopy system of this invention provides real-time, non-invasive temperature measurements of samples in-vivo or for other applications.

What is needed is a diagnostics technique for malignant melanoma that is objective and reliable, non-invasive, has low cost, and out-performs the dermatologist's sensitivity and specificity for the measurement. It is also desired that skin conditions such as Squamous cell carcinoma, seborrhoeic keratosis, and pigmented Nevi can be determined and differentiated from one another, using this technique. Furthermore, it is necessary to establish a "gradation" criterion to determine the level of malignancy detected at a given point. This criterion should have clinical validation, and ultimately should be addressed with a single-cell spatial resolution.

It is also necessary to obtain a time resolution of the measurement that is within 1 sec. This includes not only the duration of the data collection procedure, but also the processing of the signal, using dPCA or another suitable algorithm. Further, it is needed to provide the capability of building-up the system into an image-based diagnostics tool that renders 3-dimensional, histo-pathologically qualified information. This could eventually be incorporated into a "tumor removal" apparatus. Further implementation of a rapid-measurement device also includes micro-fluidic chips, where single cell resolution is paramount.

The embodiments included in this disclosure will be more completely understood in conjunction with the following detailed description taken together with the drawings.

DETAILED DESCRIPTION

The following detailed description is meant to be illustrative only and not limiting. Other embodiments of this invention will be obvious to those skilled in the art in view of this description.

In accordance with this invention a Raman spectroscopy device architecture is provided that combines a high speed time-division optical sampling engine with a unique data processing algorithm, discrete Principal Component Analysis (dPCA), in order to produce time-resolved, accurate Raman measurements with low signal levels. A variety of specific embodiments can be provided to implement the invention. The invention significantly decreases the sample processing time while increasing the number of material samples which can be processed at one time. This invention also improves the environmental ruggedness of the device while significantly decreasing the implementation cost.

Stokes Radiation Time-Multiplexing

Figure 1A:
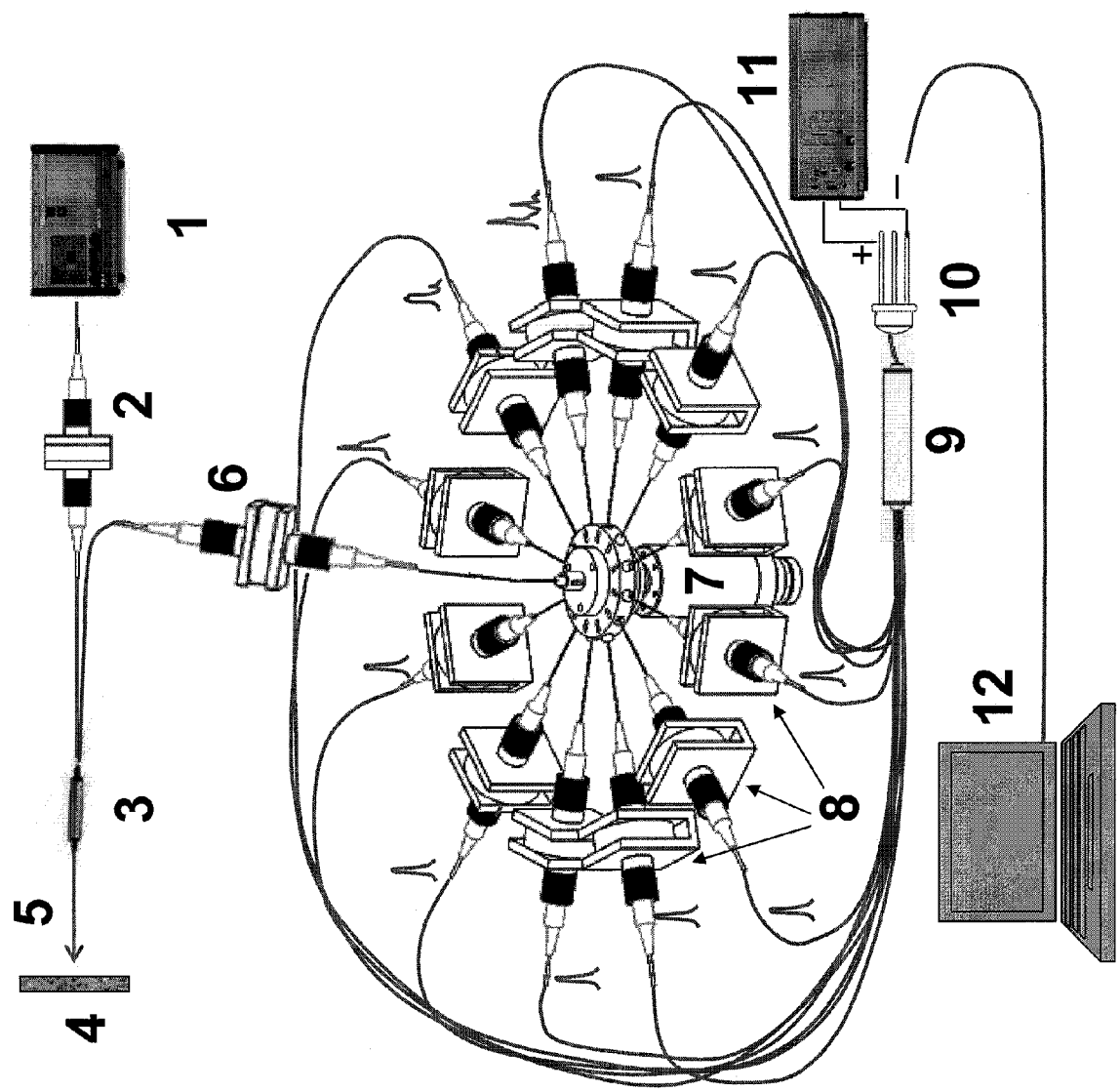
FIG. 1a shows a fiber delivery collection system with an optical circulator in accordance with this invention.

Referring to FIG. 1a, one embodiment of this invention employs a rotary switch such as disclosed in co-pending patent application Ser. No. 11/185,137 filed Jul. 20, 2005 based on provisional application No. 60/589,454 filed Jul. 20, 2004, both assigned to Neptec Optical Solutions, Inc., the assignee of this application. These two applications are hereby incorporated by reference in their entirety. This rotary switch essentially acts as a time-division multiplexing device.

In the structure of FIG. 1a, according to one of the embodiments of the present disclosure, light from a pump laser 1 (or other source such as a SLED (a "super-luminescent light emitting diode") or a gas emission lamp using halogen gases, or equivalent) illuminates a material sample 4 to be interrogated. Light back-scattered from the sample (called information light or "Stokes radiation") contains specific information about the chemical and physical make up of the material being interrogated. Hereafter, the term "Stokes radiation" will be used to mean the same as "information light", which is light scattered from the sample as a result of light from source 1 impinging on sample 4.

In the embodiment of FIG. 1a, the optical delivery of the light from the illumination source and the optical collection of the Stokes radiation are performed through the same fiber 5 (sometimes called a "waveguide"). The light from source 1 to be incident on sample 4 is first passed through narrow band-pass filter 2 to remove spurious radiation outside the desired bandwidth and is then transmitted to the sample through optical fiber 5. Stokes radiation scattered from sample 4 is also carried by waveguide 5 and is directed through an optical circulator 3 to a notch filter 6 to remove spurious information and into the z-axis of the device body. Notch filter 6 blocks the transmission of the residual back-scattered illumination light into the time-division multiplexing device 7. Notch filter 6 can be a multilayer interference filter, a colored glass filter or an absorption cell (typically from an alkali metal vapor such as Rb or Cs). Taken together, the delivery/collection fiber 5, optical circulator 3 and notch filter 6 comprise and will be referred to as the system "probe".

Optical circulator 3 is a well-known optical device with three channels wherein each channel allows the passage of light in a specific direction. In the system of FIG. 1a, circulator 3 lets light pass from the light source 1 to the sample 4 and on the third channel of the circulator 3 lets light scattered from the sample travel back from the sample 4 into the spectrometer and only in that direction. Optical circulators suitable for use with this invention are commercially available from a number of fiber optic device companies such as Optics for Research, located at Caldwell, N.J.

The light from optical circulator 3 is passed through a notch filter 6 which blocks and thus removes light at the main frequency of the light source 1. Filter 6 will pass light at frequencies other than the frequency of light from source 1. The light that passes through filter 6 impacts a motor-driven, rotating prism 13 which can be of a type shown, for example, in co-pending patent application Ser. No. 11/185,137 filed Jul. 20, 2005 (published as U.S. Publication No. 2006/0072873 A1) incorporated by reference above. The mirrored surface of prism 13 reflects the incoming light through filters 8-1 to 8-12 into one of several waveguides 18-1 to 18-12 arranged circularly in a plane perpendicular to the z-axis of rotation and centered about the z-axis of rotation. While twelve (12) waveguides 18-1 through 18-12 are shown arranged in a circle in a plane around the rotating prism 13, of course, a smaller or larger number of waveguides can be so arranged if desired. For example, in some embodiments 20 to 100 waveguides will be so arranged around the circumference of the rotating prism 13 within a plane to enable the system to determine at least 20 to 100 characteristics of the sample being analyzed.

The rotation of the prism 13 sweeps the Stokes radiation beam across the inputs of the several waveguides 18-1 to 18-12 creating a "time multiplexing" of the single Stokes radiation beam. Thereby, each waveguide receives a time slice of the original optical information signal (i.e. the Stokes radiation). Each waveguide 18-$i$ (where i is an integer varying from 1 to 12 in FIG. 1a or from 1 to N when N filters and waveguides are placed around the circle in the plane perpendicular to the z-axis of rotation) is associated with a specific optical filter 8-$i$ which is selected to transmit only a portion or selected portions of the broad wavelength range contained within the Stokes radiation. Each optical filter 8-$i$ can be, for example, a molecular filter or an interference filter. The filtered Stokes radiation passing into waveguides 18-1 to 18-12 is then directed through multiplexer 9 to a single optical detector 10 and into electronic analytical equipment, such as a computer, 12 for processing.

Electronic pulse generator 11 causes the photo-sensitive element 10 (which might be an avalanche photo-detector, a photodiode, a photomultiplier or a micro channel plate, for example, or any other type of photo-sensitive element), to be turned on and activated whenever a signal from waveguide 18-$i$ strikes the photo-sensitive element 10. The pulse generator 11 essentially synchronizes the operation of photo-sensitive element 10 with the arrival of a signal scattered from prism 13 through a corresponding waveguide 18-$i$.

The filters 8 in front of waveguides 18 are each selected to allow certain light representative of certain types of components which might be present in the sample 4 to be transmitted from the probe to the optical fibers 18-1 through 18-12 to the multiplexer 9. The multiplicity of filters 8-1, to 8-12 spectrally decompose the Stokes radiation and separate it into a timed sequence of pulses. These pulses are re-directed to a single photo-sensitive element 10 via a multiplexing element 9.

Multiplexer 9 (which might be a single mode fiber, a multimode fiber, or a photonic crystal fiber (PCF) depending on the desired numerical aperture, bandwidth and transmission loss of the device) will pass the signal being transmitted on the corresponding fiber 18-i when information light scattered from the rotating prism 13 impacts the corresponding waveguide 18-i.

The speed of rotation of prism 13 determines the frequency with which signal processing unit 12 (which might, for example, include a digital signal processor, certain recognition algorithms and a computer for carrying out the data processing) receives the signals from each of the waveguides 18-1 through 18-12 on FIG. 1a. By increasing the speed of rotation of the prism 13, the number of samples $S_1, S_2, \ldots S_N$, for example, capable of being processed by the signal processing unit 12 in a given time can be increased provided the speed of processing within processing unit is capable of analyzing the samples as they are delivered to the processing unit 12. The speed of the processing unit 12 can be adjusted by including several processing units in parallel if necessary.

Figure 1B:
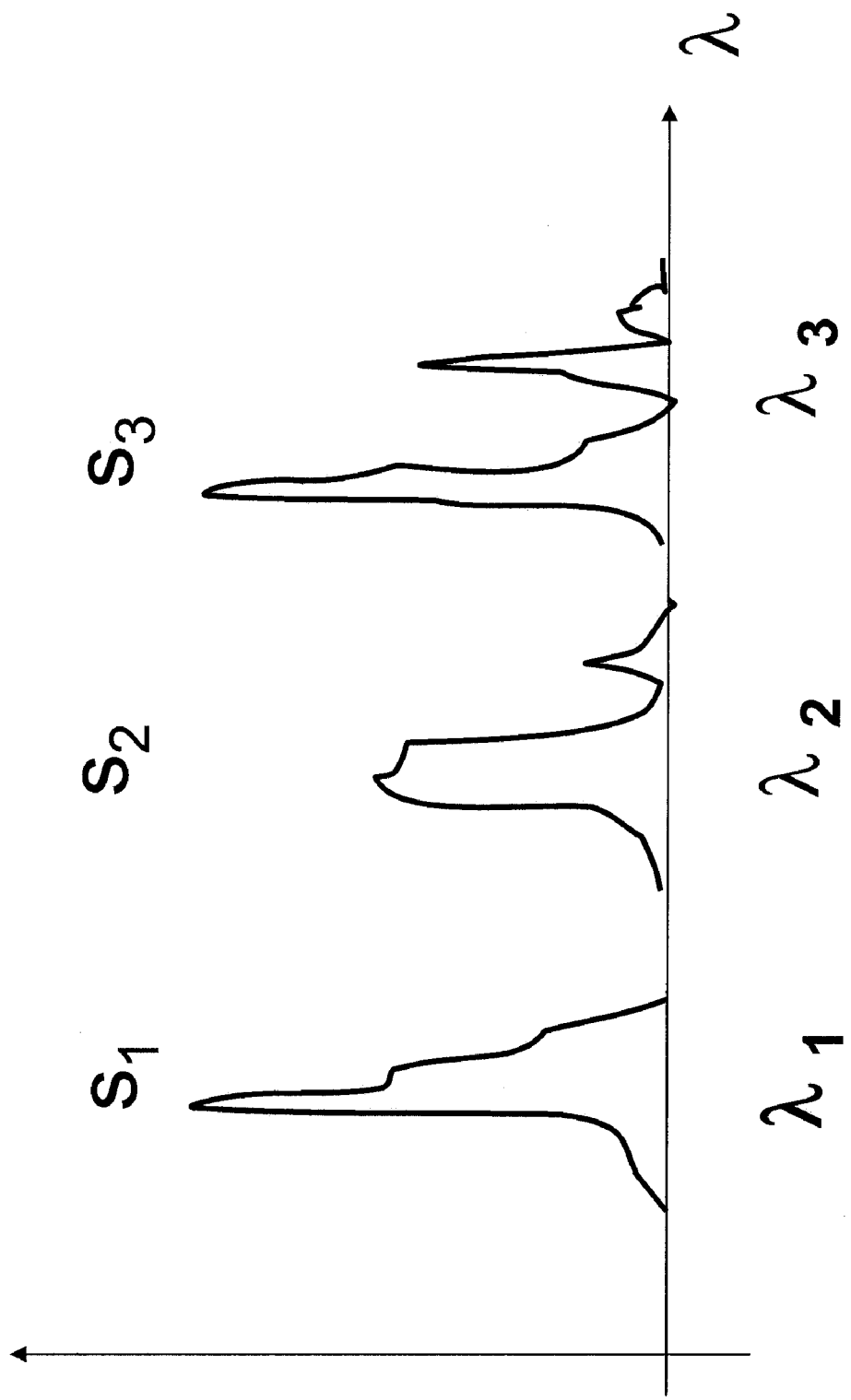
FIG. 1b shows a schematic representation of a Raman signal as a function of wavelength, according to some embodiments of the present invention.

FIG. 1b shows the spectrum of three Raman signals $S_1$, $S_2$ and $S_3$, according to their wavelength. In some embodiments of the present disclosure, Raman signals $S_1$, $S_2$ and $S_3$ may be associated to different components or chemical substances forming part of a given sample, or may be different Raman bands emitted by the same component or chemical substance forming part of a given sample. More generally, Raman signals $S_1$, $S_2$ and $S_3$, may include a combination of different Raman bands emitted by a single component, and Raman signals produced by different components or chemical substances forming part of a given sample. Further, the number of Raman bands shown in FIG. 1b is not restrictive to three, but could be smaller, e.g. only 1 Raman band, or much larger than 3, e.g. 10, 20 or even more.

The Raman bands shown in FIG. 1b, may also form a continuum spectrum, as opposed to a discrete set of Raman emission bands, or a combination of a continuum portion of a Raman spectrum and any number of discrete Raman bands.

Figure 1C:
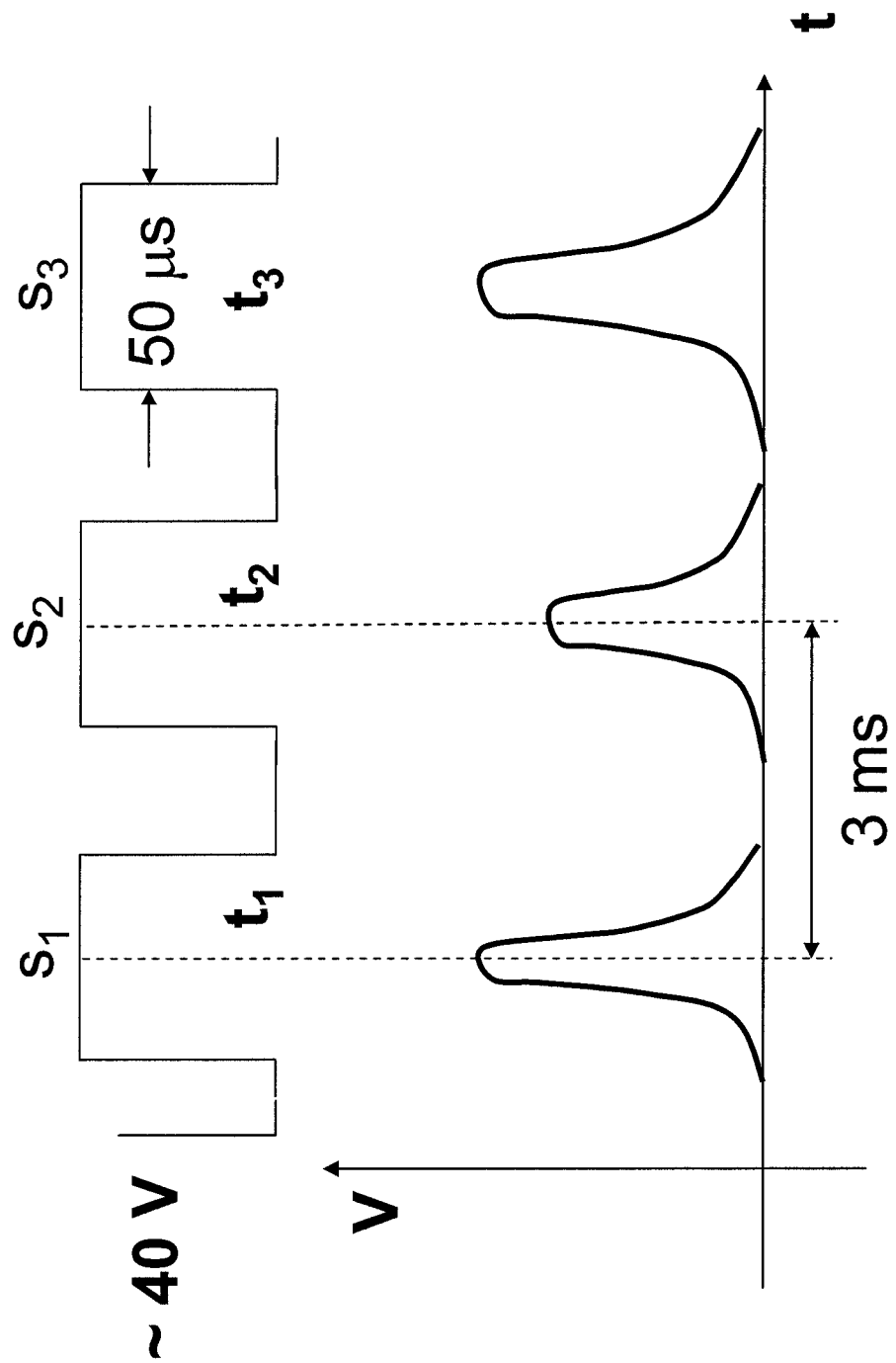
FIG. 1c shows a schematic representation of a Raman signal as a function of time, according to some embodiments of the present invention.

FIG. 1c shows the spectrum of the same three Raman signals shown in FIG. 1b, as obtained in some of the embodiments of the present disclosure, namely $S_1$, $S_2$, and $S_3$, according to the times at which these three signals are made available through waveguides 18-1, 18-2 and 18-3 in sequence. As shown in FIG. 1c, each signal $S_i$ reaches an adjacent waveguide 18-i about 3 milliseconds after the preceding signal has reached its waveguide. Thus, if signal $S_1$ reached waveguide 18-1 at time 0, signal $S_2$ would reach waveguide 18-2 at a time 3 milliseconds thereafter and signal $S_3$ would reach waveguide 18-3 at a time 6 milliseconds after the first signal $S_1$ reach waveguide 18-1. Three millisecond time between each of the signals with eight different signals being processed corresponds to $41\frac{2}{3}$ revolutions per second. The actual revolutions per second will depend upon the number of samples to be generated which corresponds to the number of waveguides 8 which are employed on the circle in the plane perpendicular to the z-axis of the system shown in FIG. 1a.

Detector Time-Multiplexing

The detector (made up of photo-sensitive element 10, electronic pulse generator and synchronizing circuit 11 and the signal processing unit 12) is electrically turned off and optically isolated until it is required to be active to sense the weak information input signal. The position of the prism 13 with the Stokes radiation relative to a specific waveguide 18-i with filter 8-i is time correlated by electronic synchronizing circuit 11 with the electrical reactivation of the photo-sensitive element 10 in the detector; therefore, element 10 electrically turns on exactly when the Stokes radiation pulse reaches it. This innovation permits accurate signal timing and enables the photo-sensitive element 10 of the detector components 10, 11 and 12 to be at maximum optical sensitivity when light impacts element 10. The combination of the above procedures results in a broad band data collection, within the duration of one rotation cycle of the prism 13.

One implementation employs pump laser 1 illuminating a sample 3 (which might consist of a solid, a liquid, or a gaseous material embedded in a pipeline, container, or in free space) and multi-mode optical fibers 18-1 to 18-12 as waveguides for directing the different light paths. Back-scattered light is connected to an optical collimator 3 (input collimator) which is mounted on top of the device body 15, along the axis of rotation 16 (also called the z-axis) of the time-division multiplexer 7. A 7,000-rpm motor (not shown) with a 7 mm×7 mm prism 13 is surrounded by the array of twelve (12) optical collimators 8-1 to 8-12 robotically aligned and mounted on a ceramic cylindrical shaped body (optical bench). These collimators 8-1 to 8-12 are positioned on a plane perpendicular to both the input collimator 3 and the axis of rotation 16 of the motor shaft.

Along the optical path of each collimator, a wavelength specific filter 8-1 to 8-12 is placed, creating twelve (12) optical "channels". Each channel filters a different region of the input spectrum allowing the detector 10 to sense only the selected wavelengths. The collection of the ceramic body, collimators, filters 8-1 to 8-12 rotating mirrored prism 13, and motor and ancillary structures comprises the rotary optical switch device 15 (FIG. 1a).

The multiple collimators direct the filtered light channels into a detector 10 via multi-mode optical fibers 18-1 to 18-12 whose output signals are multiplexed to impact the surface of a single, ultra-sensitive photo-detector device 10 (e.g. an avalanche photo-detector, or APD). The detector 10 is electrically pulsed on and off via a pulse generator 10 and electrically synchronized to the position of the motor shaft, enabling the coordination of the rotating prism 13 with the electrical activation of the photo-detector 10. By turning on and off the detector 10, Raman spectroscopy is possible with lower level signals than heretofore used because keeping detector 10 off when no signal light (i.e. Stokes radiation) is incident on the detector 10 keeps the noise level down. This makes it possible for detector 10 to pick up weaker Stokes radiation than in prior art systems.

Different types of detectors 10 can be used. A highly sensitive APD can be used (typically Si, GaAs or InGaAs material type, depending on the wavelength region to be measured), operated marginally (3-4%) above the internal breakdown-voltage of the device (~40 V) to minimize noise and maximize sensitivity to light (Geiger-mode operation).

Other embodiments can use photomultiplier tubes, to operate in the UV-visible spectral range. By sending only selected, pre-filtered light into the detector 10 and by only powering the detector 10 when the light pulse is about to impact detector 10, an overall reduction in both electrical and optical noise of significant magnitude is achieved allowing for a collection of spectral information which is 2-3 orders of magnitude faster than conventional techniques. The rotary optical switch 15 combined with the optics 10 and electronics 11, 12 described above provides a vastly improved Raman spectrometer instrument.

The signal from the photo-sensitive element 10 is amplified, filtered, and processed electronically by signal processing unit 12. Signal processing can be performed by analog or digital electronics, or a combination of both. A digital signal processor (DSP) can be implemented as a very compact and fast device to perform such operations. The combination of multiplexing element 9, photo-sensitive element 10, pulse generator 11, and signal processing unit 12 will be called the "back end" of the Raman spectrometer system described herein.

An additional embodiment uses a pump laser through a multi-mode fiber that also acts as a collection mechanism where the return spectra is separated from the transmitted spectra via the use of a circulator or equivalent.

Figure 2:
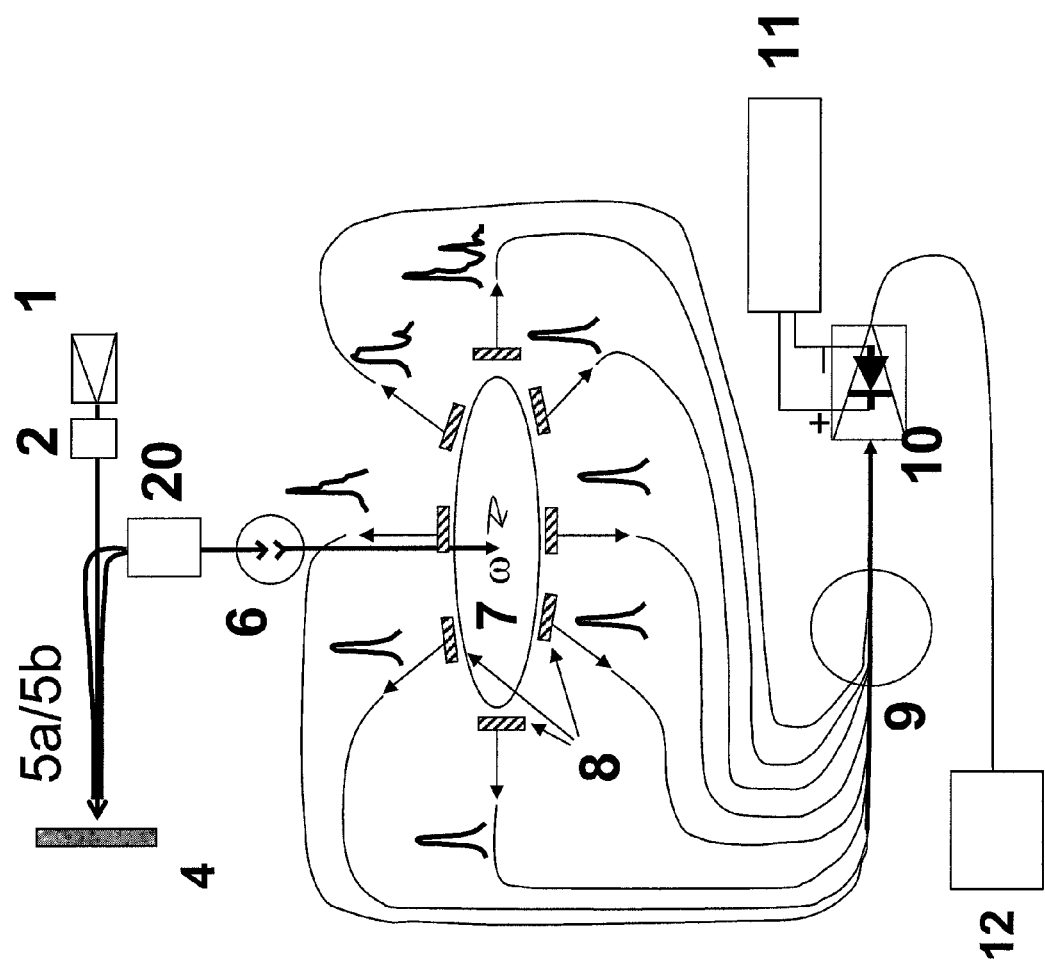
FIG. 2 shows a photonic crystal fiber delivery system in accordance with this invention.

FIG. 2 shows a photonic crystal fiber delivery system using a fiber bundle collection. In FIG. 2, many of the components are the same as or similar to those in FIG. 1a but for simplicity will be shown schematically rather than in the detail shown in FIG. 1a. (A similar approach is taken with respect to the remaining FIGS. 3, 4, 5a, 5b and 6.) The system of FIG. 2 uses a different probe than the system in FIG. 1a. The probe of the system in FIG. 2 delivers the light from the illumination source 1 to the sample 4 by one optical fiber 5a and collects the Stokes radiation scattered from the sample 4 by different optical fibers 5b. The delivery of the light to sample 4 is done by a photonic crystal fiber to reduce the modal area of illumination on the sample 4. The Stokes radiation is delivered by a set of optical fibers around the delivery fiber to maximize the efficiency of collection of the Stokes radiation. Multiplexer 20 collects the signal from the fiber bundle and directs it to the notch filter 6, the time division multiplexer 7, the filers 8, a multiplexer 9 and the photo-sensitive element 10. The remainder of the back end is similar to what is shown in FIG. 1a and includes the electronic pulse generator 11 and the signal processing unit 12. Another difference between the system of FIG. 1a and the system of FIG. 2 is the use of multiplexer 20 in the optical channel between the scattered light from the sample 4 and the notch filter 6 located in the path followed by the Stokes radiation to prism 13 in the time-division multiplexing device 7. The numbers set forth in the remainder of the structure in FIG. 2 are identical with the numbers set forth in FIG. 1a to the extent these components are the same. Therefore, these components operate as described in connection with FIG. 1a.

Figure 3:
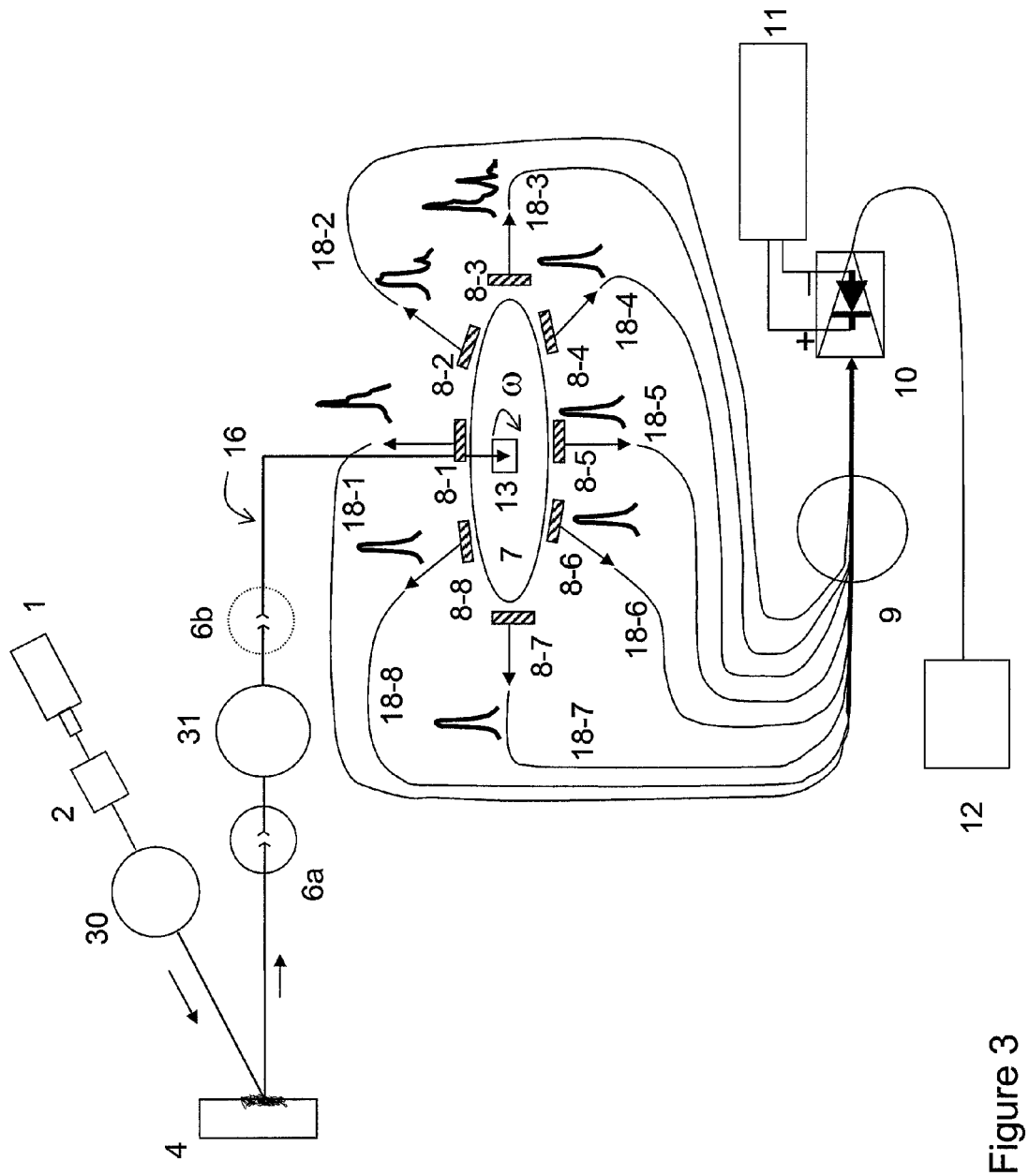
FIG. 3 shows a free space delivery and collection system in accordance with this invention.

FIG. 3 shows a system which uses a probe that includes a free space delivery component. The system shown in FIG. 3 includes many of the components shown in FIGS. 1a and 2. Unless otherwise specified, identical components are numbered identically as in FIGS. 1a and 2. New components are numbered differently. The system shown in FIG. 3 can be used in near field collection (microscopy) or far field collection (remote sensing) regimes.

In FIG. 3, an illumination source 1, which could be a laser or bright lamp, for example, provides light (such as CW pump radiation) which passes through narrow band-pass filter 2 to free space delivery optics 30 which could be a lens, a parabolic mirror or similar structure. From optics 30, the focused light impacts on sample 4 at a selected position. The scattered light (i.e., the Stokes radiation) passes through notch filter 6a (which could be, for example, an interference grating, colored glass, an absorption cell or a fiber grating). Notch filter 6a, if desired, can be embedded in fiber or located in free space.

The signal from notch filter 6a is then transmitted in free space to collection optics 31 (which might include appropriate combinations of selected ones of lenses, mirrors, prisms and apertures, for example). Optics 31 couples the scattered Stokes radiation into an optical fiber 16 that directs the light to the time-division multiplexing device 7 (as described above). At least part of optical fiber 16 is located on the axis of rotation of the time division multiplexing device 7. Notched filter 6a can, if desired, be replaced by an identical notched filter 6b located after optics 31 rather than before optics 31.

Prism 13 reflects the light transmitted along optical fiber 16 to an appropriate one of filters 8-1 through 8-8. Filters 8-1 through 8-8 can be any one of a number of different types of filters such as molecular filters, or interference filters, for example as described above in conjunction with FIG. 1a and FIG. 2. The signals from filters 8-1 through 8-8 are sent on optical fibers 18-1 through 18-8 to a multiplexer 9 where each of the signals then is transmitted to light detector 10. Electronic synchronization circuit 11 activates light detector 10 before each of the signals from the corresponding filters 8-1 through 8-8 reach detector 10 and thus synchronizes the turning on of detector 10 with the application of the signal scattered by prism 13 to the appropriate one of filter 8-1 through 8-8. The system otherwise operates just as the system shown in FIGS. 1a and 2.

Figure 4:
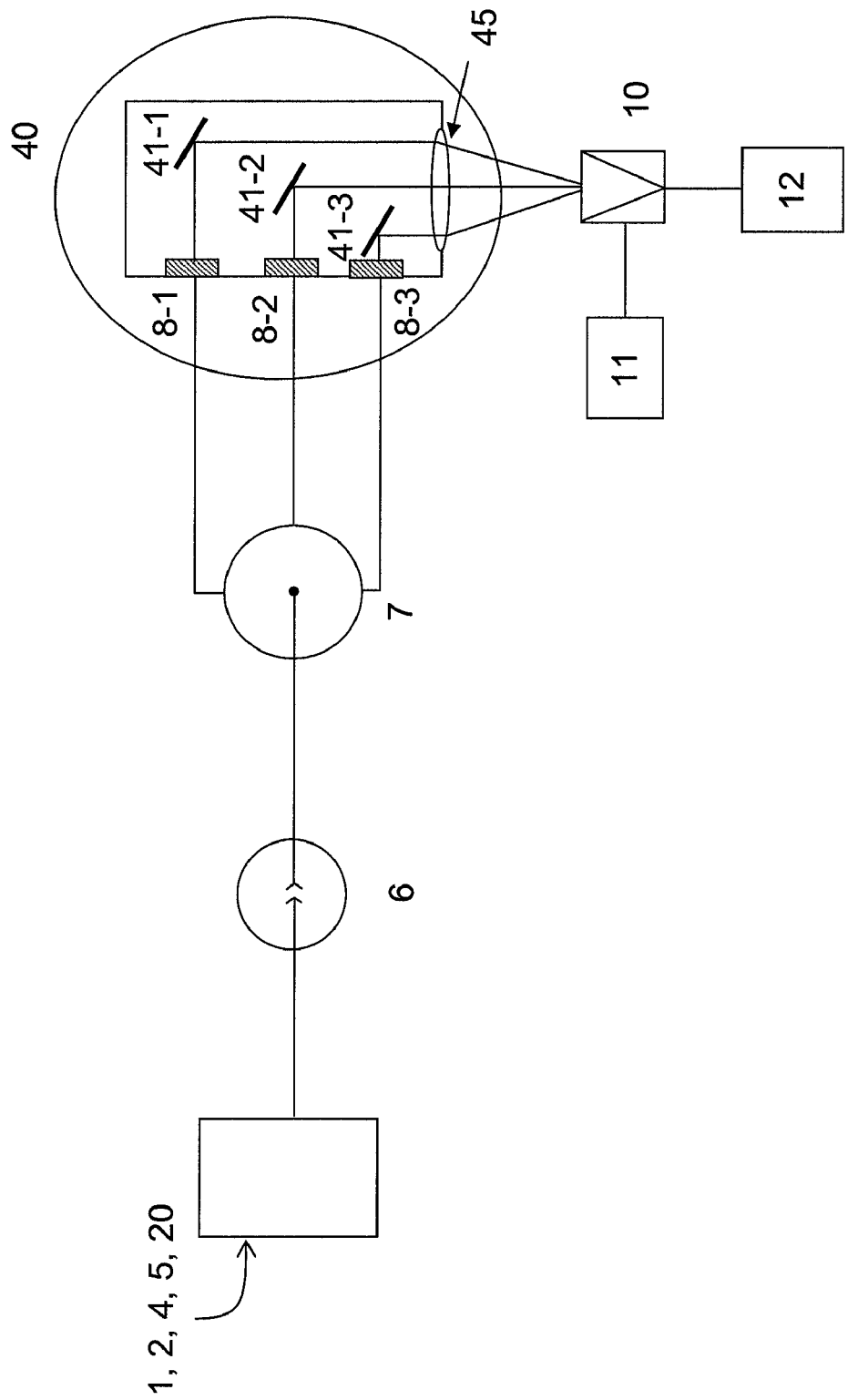
FIG. 4 shows a free space signal collection system utilizing the principles of this invention.

FIG. 4 shows another embodiment of this invention with a modified back end. An illumination source 1 (which can be a laser or bright lamp, for example), a narrow band-pass filter 2, a multiplexer (which is of a well-known construction) 20, a sample 4 and a delivery fiber 5 (which, for example, can be a photonic crystal fiber (PCF)) operate in much the same way as shown in FIGS. 1a, 2 and 3. In FIG. 4, these components are depicted in the box with the numbers 1, 2, 4, 5, 20. The information signal scattered from the sample 4 is transmitted to the notched filter 6 (which again can be an interference grading, colored glass or an absorption cell, for example) and then to time-division multiplexing device 7. The time-division multiplexing device 7 can be, for example, the rotating disk with a prism 13 on it as shown in FIGS. 1a, 2 and 3. From this disk, however, the signal is sent in a manner described above in conjunction with FIGS. 1a, 2 and 3 to various molecular or interference filters 8-1, 8-2 and 8-3 as shown. Of course, other numbers of filters can be used if desired. Each filter 8-1, 8-2 and 8-3 is arranged in a structure known as a free space multiplexer box 40 which can be fabricated of any acceptable material such as ceramic, metal, or plastic. For example, Box 9 contains reflecting elements 41-1, 41-2, and 41-3 (for example, mirrors) for reflecting the corresponding signals from filters 8-1, 8-2 and 8-3, respectively, to a focusing lens 45. The signal from lens 45 then is sent to a photo-sensitive element 10 which operates as described in the previous description of system shown in FIGS. 1a, 2 and 3. The detector 10 sends its signal to signal processing unit 12. Electronic pulse-generator and synchronization circuit 11 operates to turn on the detector 10 in response to the signals from multiplexing device 7 hitting the respective ones of mirrors 41-1 through 41-3 and thereby in time sequence as shown in FIG. 1c striking detector 10. The system in this respect operates as described above.

Figure 5A:
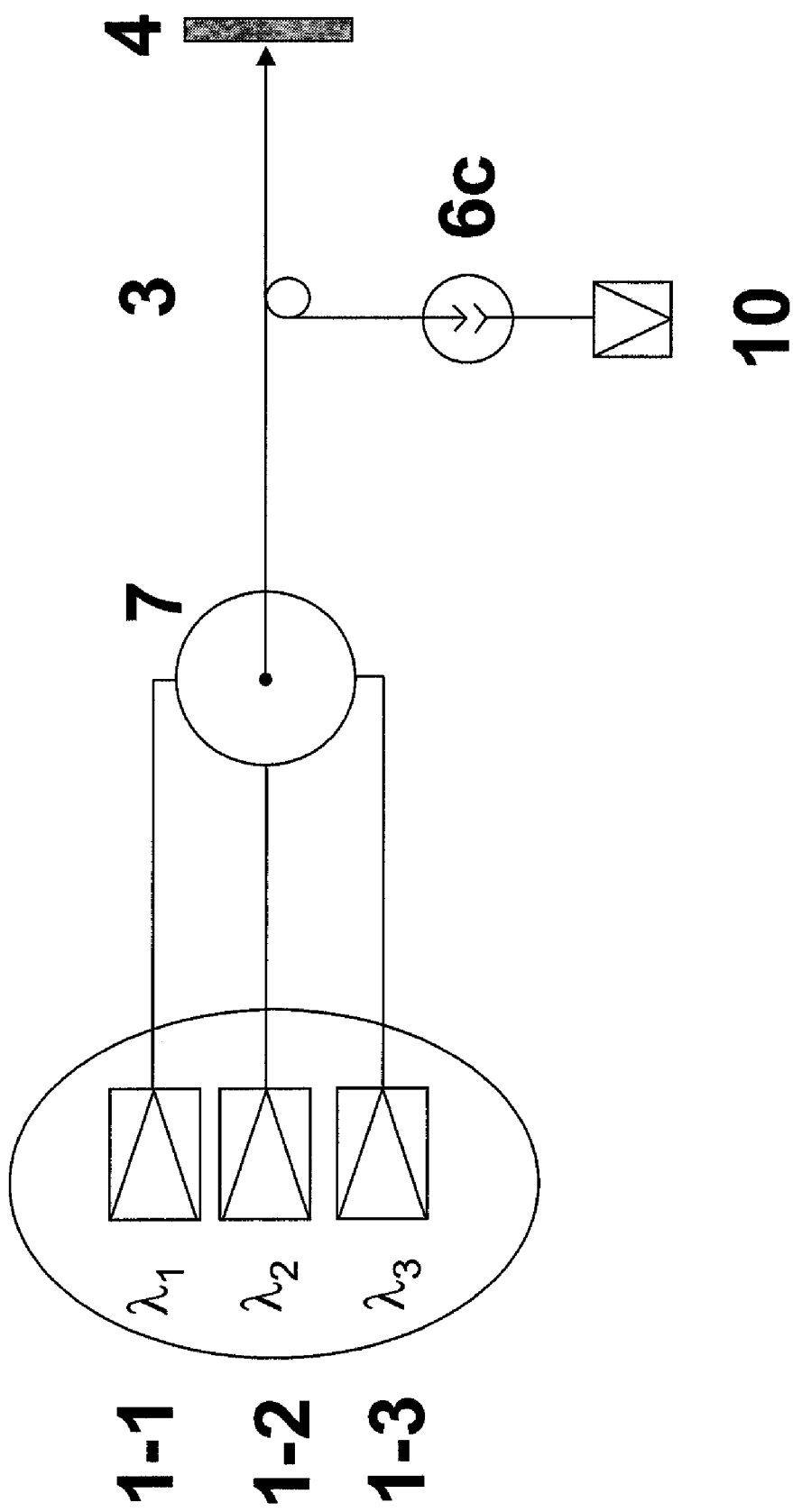
FIG. 5a shows an embodiment of this invention using multiple illumination sources and multiple pump lasers.

FIG. 5a illustrates a system for Raman spectroscopy which employs multiple lasers. Thus, multiple lasers 1-1, 1-2 and 1-3 provide signals of different wavelengths $\lambda_1$, $\lambda_2$, $\lambda_3$, respectively. These signals are transmitted to a time-division multiplexer which has thereon an optical system which allows these signals to be transmitted in sequence to a sample 4. The Stokes radiation scattered from sample 4 is sent to optical circulator 3 and from there is sent to a notched filter 6c which blocks the signals with wavelengths $\lambda_1$, $\lambda_2$, and $\lambda_3$ but which passes the stokes radiation associated with these wavelengths. Optical filter 6c, although a blocking filter for the wavelengths $\lambda_1$, $\lambda_2$, and $\lambda_3$, is a single band-pass or band-block filter for the Stokes radiation. This combined filter is made possible by the large spectral range between the illumination radiation and the Stokes radiation in most Raman signals.

Photo-sensitive element 10 then receives in sequence Stokes radiation signals associated with wavelengths $\lambda_1$, $\lambda_2$, $\lambda_3$ and is readily turned on in synchronicity with the operation of time-division multiplexer 7 to transmit the signals to a processing unit 12 which operates as described above in conjunction with FIGS. 1a, 2 and 3.

Figure 5B:
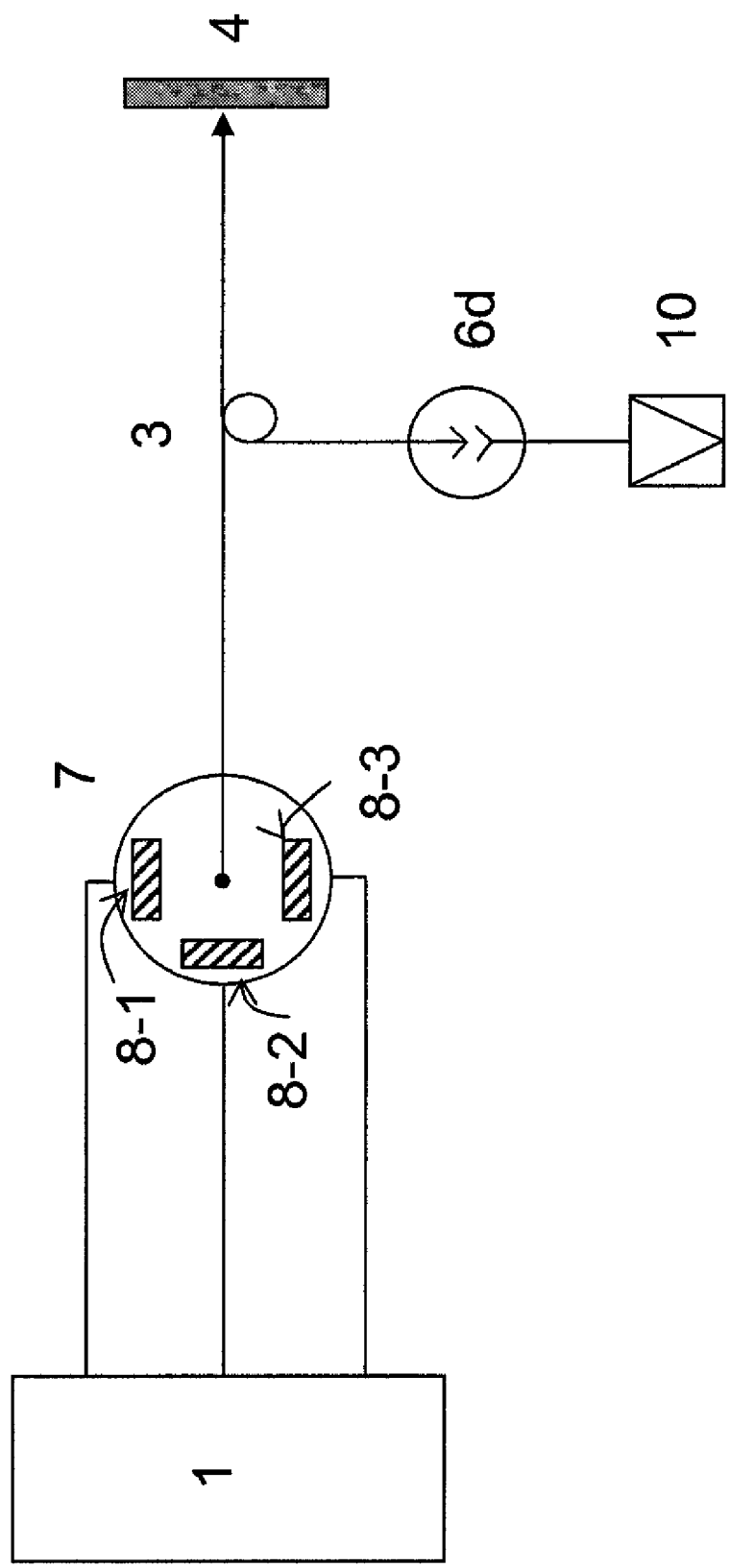
FIG. 5b shows an embodiment of this invention using multiple illumination sources and an emission lamp with filters.

FIG. 5b shows a similar structure as in FIG. 5a except here a single broadband light source 1 (for example, a metal-halogen light source, or a Mercury gas lamp, or a Xenon arc lamp, or a Neon arc lamp) provides light which is then transmitted through filters 8-1, 8-2 and 8-3 which are part of time-division multiplexer 7. As time-division multiplexer 7 rotates, specific pulses of light are passed along the path from multiplexer 7 to sample 4 in a reverse direction from the direction of the light transmitted in the systems shown in FIGS. 1a, 2, 3, 4 and 5a. The Stokes radiation scattered from sample 4 is passed through optical circulator 3 and then through a filter 6d which passes $\lambda_1$, $\lambda_2$ and $\lambda_3$ to the photo-sensitive element 10. Photo-sensitive element 10 is again activated by electronic pulse generator 11 (not shown in FIG. 5b) which synchronizes the turning on of detector 10 with the incidence of the light from filters 8-1 through 8-3 on sample 4. Processor 12 (also not shown in FIG. 5b) then processes the output signal from detector 10 to determine the presence of selected components in the sample.

Figure 6A:
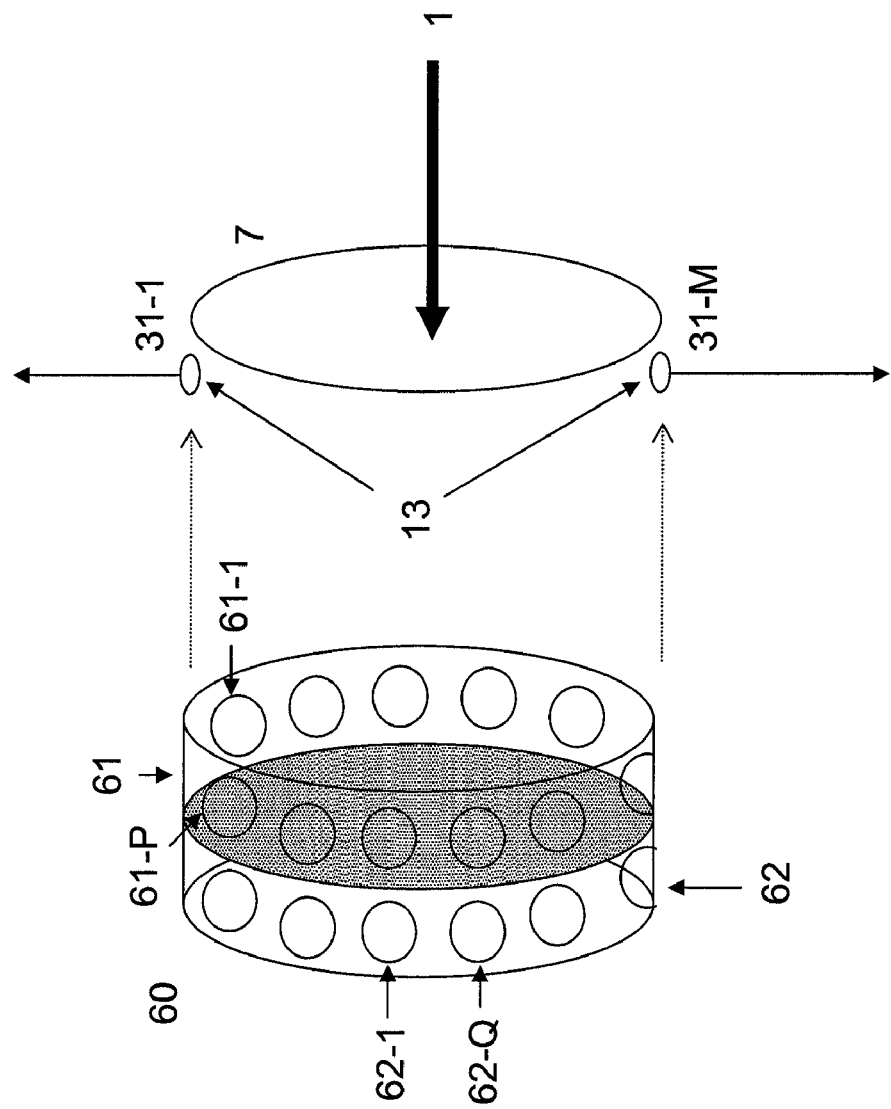
FIG. 6a shows a technique for implementing coarse and fine spectral coverage.
Figure 6B:
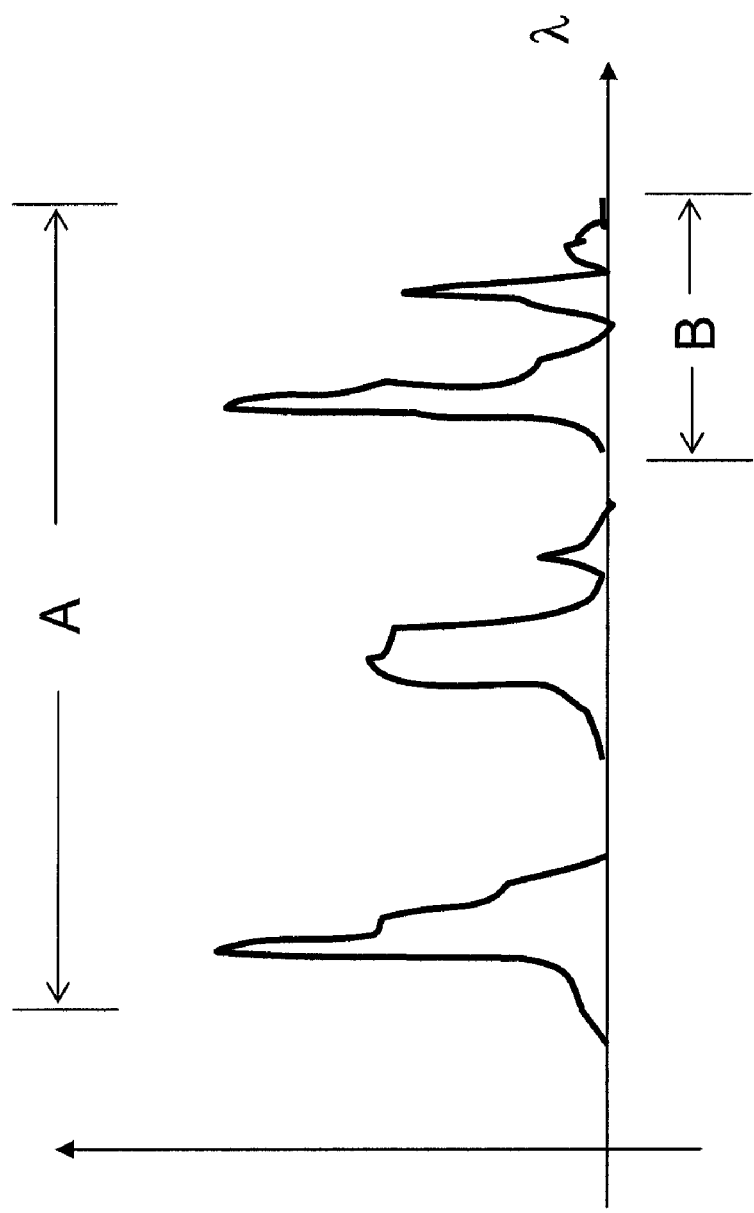
FIG. 6b shows a coarse and a fine spectral range used to analyze a sample according to some embodiments of the present invention.

FIG. 6a illustrates a structure which provides coarse and fine spectral coverage. Collected and filtered light from the sample 4 is passed through time-division multiplexer 7 which operates as discussed above in conjunction with FIGS. 1a, 2 and 3. Collimators 31-1 to 31-M (where M is an integer representing the number of channels in multiplexer 7) send this light to auxiliary channels. Then a drum 60 with a coarse set of filters 61-1 to 61-P and a fine set of filters 62-1 to 62-Q, where P and Q are each a selected integer representing the maximum number of coarse and fine filters, respectively, is inserted into multiplexer 7 such that the light reflected from the prism 13 in time-division multiplexer 7 is then sent through in time sequence each filter in the coarse set of filters 61-1 to 61-P to provide a broadband sensitivity to light. By further inserting the drum into multiplexer 7, a narrow set of filters 62-1 to 62-Q which provide narrow band sensitivity to light, is placed between the rotating prism 13 and the transmission channels to the light detector. The bandwidth associated with the coarse set of filters 61 is shown in FIG. 6b within the bracketed range "A" whereas the bandwidth associated with the fine set of filters 62 is shown bracketed with the range "B" in FIG. 6b. This particular structure allows the system to make a fast determination that there is a signal of interest within the broadband "A" and then determine using the fine set of filters whether or not that signal of interest actually contains information with respect to a component of interest.

The drum shown in FIG. 6 has two sets of filters, but more than two sets of filters can be employed in this embodiment if desired. The use of a plurality of filter sets allows the system to cover a wider spectral range in the Stokes radiation domain or possibly to increase the spectral resolution for a given feature as discussed above.

The particular set of filters to receive the light from the multiplexer 21 is moved into position by moving the drum on which the filters are mounted laterally along its cylindrical axis by means of mechanical components of well known design but not shown here for clarity. The coarse set of filters or the fine set of filters are actually moved laterally along the z-axis of the time division multiplexer 21 until the particular ring of filters (either coarse or fine) is spaced precisely between the collimators 31-1 through 31-M and the rotating prism 13 associated with the time division multiplexer 21. As a result, as the time division multiplexer rotates, the beam from the prism 13 is filtered through either the coarse set or the fine set of filters and the particular collimator associated with each of the filters in the coarse set or the fine set will then pass the signal through the corresponding waveguide to the signal processing structure as described above, such as to processor 12 in FIG. 1a. Of course, the width W of each band of filters (i.e. the width of the coarse set 41-1 to 41-P and the width of the fine set 42-1 to 42-Q must be such that when taken together, the distance of the collimators 31-1 through 31-M from the plane of the time division multiplexer 21 on which the collimators 31 are mounted is sufficient to allow the fine set of filters 42-1 to 42-Q to actually be located between the collimators 31 and the rotating prism 13 such that the signal from the rotating prism 13 will in fact impact appropriately on each filter in the fine set of filters.

The system shown in FIG. 6 is highly convenient in applications where a layered response is necessary in order to activate an alarm, as in the case where the presence of a noxious substance is ultimately verified by a refined spectral analysis.

Description of the Data Processing Algorithm

The algorithm used for processing the electrical signal from the photo-sensitive unit is a discrete principal component analysis procedure (dPCA) which will be outlined in the following. The amount of Raman power, $P_R(v_i)$, produced by frequency mode, $v_i$, from a given scattering material, upon the incidence of pump radiation with power, $P_P$, is given by the following expression $$P_R(v_i) = P_P \cdot \varepsilon \chi_i \rho l \left(\frac{\partial \sigma}{\partial \Omega}\right)_{\lambda_R} \Delta \Omega \tag{1}$$

where, $\varepsilon$, is the optical collection efficiency of the system, $\chi_i$ is the relative concentration of the scattering substance (a number between 0 and 1), and $\rho$, is the density of the scattering substance (g/cm$^3$), 1, is the transversal dimension of the illumination area of the sample, $(\partial\sigma/\partial\Omega)_{\lambda_R}$, is the Raman scattering cross section of the material (in cm$^2$/(gSr)), and $\Delta\Omega$ is the total solid angle of collection.

For the quantitative determination of a mixture with m different substances, assume that n different Stokes Raman spectral bands have been selected for the channels of the time-division multiplexing device. The number n has to equal or be greater than m, its exact value being application specific. Normally, n will range between just a few (3 or 4), and several tens of channels (50 to 100). The judicious selection of a limited number of spectral bands is essential for the discretization of the analysis technique to make it simple. Typical PCA algorithms make use of the whole spectrum across a broad collection band, with 100-1000 values per spectrum. Due to the lower dimensionality of the data sets (by a factor of 10-100), the number of operations to complete the algorithm is 3 to 6 orders of magnitude lower than for conventional algorithms. If $\sigma_{ij}$ denotes the normalized contribution of the Raman spectrum from substance j onto filter i, and $\chi_j$ is the relative concentration of substance j in the mixture, then the collected light intensity by the switch at channel k, $A_k$, is:

$$A_k = \sum_l \sigma_{kl} \chi_l \qquad (2)$$

The validity of Eq. (2) in the case of a Raman spectrum is supported by the linear dependence on the concentration, $\chi_j$, expressed in Eq. (1). The same statement is not true in the case of Infra-red absorption, and complicates the analysis in the case of high analyte concentrations. In general, Eq. (2) is a system of n inhomogeneous linear equations with m unknowns. The basic proposition of chemometrics is that it is always possible to find enough independent bands, n, in the Raman spectra of the substances of interest, so that Eq. (2) can be solved for $\chi$. Following the spirit of Chemical Factor Analysis,[1] we can write Eq. (2) in matrix notation as

[1] Edmund R. Malinowski; Factor Analysis in Chemistry, 3rd Edition, Wiley-Interscience, New York (2002). ISBN 0-471-13479-1.

$$A = \sigma \cdot \chi \qquad (3)$$

where, $\sigma$, is an n×m rectangular matrix. A new matrix, Z, is defined:

$$Z = \sigma^t \cdot \sigma \qquad (4)$$

Z is a square, symmetric matrix, and therefore it can be diagonalized and inverted by a unitary matrix, Q, as in:

$$Z = Q^t \cdot \Lambda \cdot Q \qquad (5)$$

where, $\Lambda$, is a diagonal matrix containing the eigen-values of Z. Finally, from Eq. (3), (4) and (5), a solution can be found for $\chi$ as $$\chi = Q \cdot \Lambda^{-1} \cdot Q^t \cdot \sigma^t \cdot A \qquad (6)$$

The matrix of eigen values, $\Lambda$, is relevant because it dissects the parameter space, $\chi$, in terms of linear combinations of its components such that their net effect in the measurement, A, can be quantified. This is accomplished by evaluating the relative magnitude of the eigen values ($\Lambda_i$). The parameter(s) that has the highest value indicates the relevant variable(s) in the problem, whereas the others give an indication of the dispersion of the data around the qualifying parameter(s).

Equation (6) is basically the equation that is used in the signal processing unit 12 to calculate the concentration of each analyte (i.e. the concentration of each different component in the sample) from the information represented by A. Each entry in vector A corresponds to a photo-detector measurement from a particular waveguide connecting to the photo-detector 10 (FIG. 1a) when a signal from a particular filter 8-i is impacting on detector 10. Thus, this particular signal as produced by detector 10 will be processed by processing unit 12 using constants which have been placed in a table in memory for access by computer 12, together with all other signals from each filter 8-i, after each cycle of the time-division multiplexing device is completed. The user would identify the particular sample being analyzed and the computer then would automatically go to a table corresponding to the possible components of that sample to determine the constants $Q \cdot \Lambda^{-1} Q^t$ and $\sigma^t$ to be used in the calculation of the concentration of each analyte which constitutes the sample. Q and $\sigma$ depend on the particular filters selected. An example set forth below will explain what the units are for each of these symbols and give therefor a calculation as would be done by signal processing unit 12 based upon a typical sample to be analyzed by the system. Example 1.

The construction of the matrix, $\sigma$, starts by selecting n band-pass filters, $f_i$, with bandwidth $\Delta \lambda_i$. The elements of the matrix are thus given by the following expression:

$$\sigma_{ij} = \kappa \int_{\lambda_i - \Delta\lambda_i/2}^{\lambda_i + \Delta\lambda_i/2} f_i(\lambda) \cdot g_j(\lambda) d\lambda; \qquad (7)$$

In Eq. 7, $f_i$ is the pass-band function for filter i, and $g_j$ is the wavelength-dependent Raman efficiency for substance j, including all its active Raman bands. The factor, $\kappa$, is a constant that relates the unit-less numbers, $\chi_j$, to the photo-detector measurements, $A_i$, in Watts, through Eq. (3). Two fundamental issues are: the number of filters to be used, and which filters to use, $f_i$ in terms of their center wavelength, $\lambda_i$, and their bandwidths, $\Delta \lambda_i$. For a given number of filters, n, the error in measurement can be proven to be inversely proportional to $\sqrt{\xi^2}$, with $\xi = \text{Det}(Z)$. Therefore, the essential step of the dPCA technique comprises the selection of a filter set {f1, f2, ..., fn} such that $\xi$ is maximized, for a given n, resulting in a value $\xi_n$. It can also be proven that $\xi_n$ grows monotonically with n. The final decision of the number of filters to be used, n, is made as a compromise between the tolerance level for the measurement error, and the architectural considerations for device construction.

[2] *Real-Time Broad-Band Measurement of Cholesterol, Collagen, and Elastin Using a Novel Rotary Switch Spectrometer*; Ricardo Claps, Roy Guynn, Wiktor Serafin, Jeff Virojanapa, Aaron Urbas, and Robert A. Lodder *Proc. SPIE* 6078, 60782G (2006).

Figure 7:
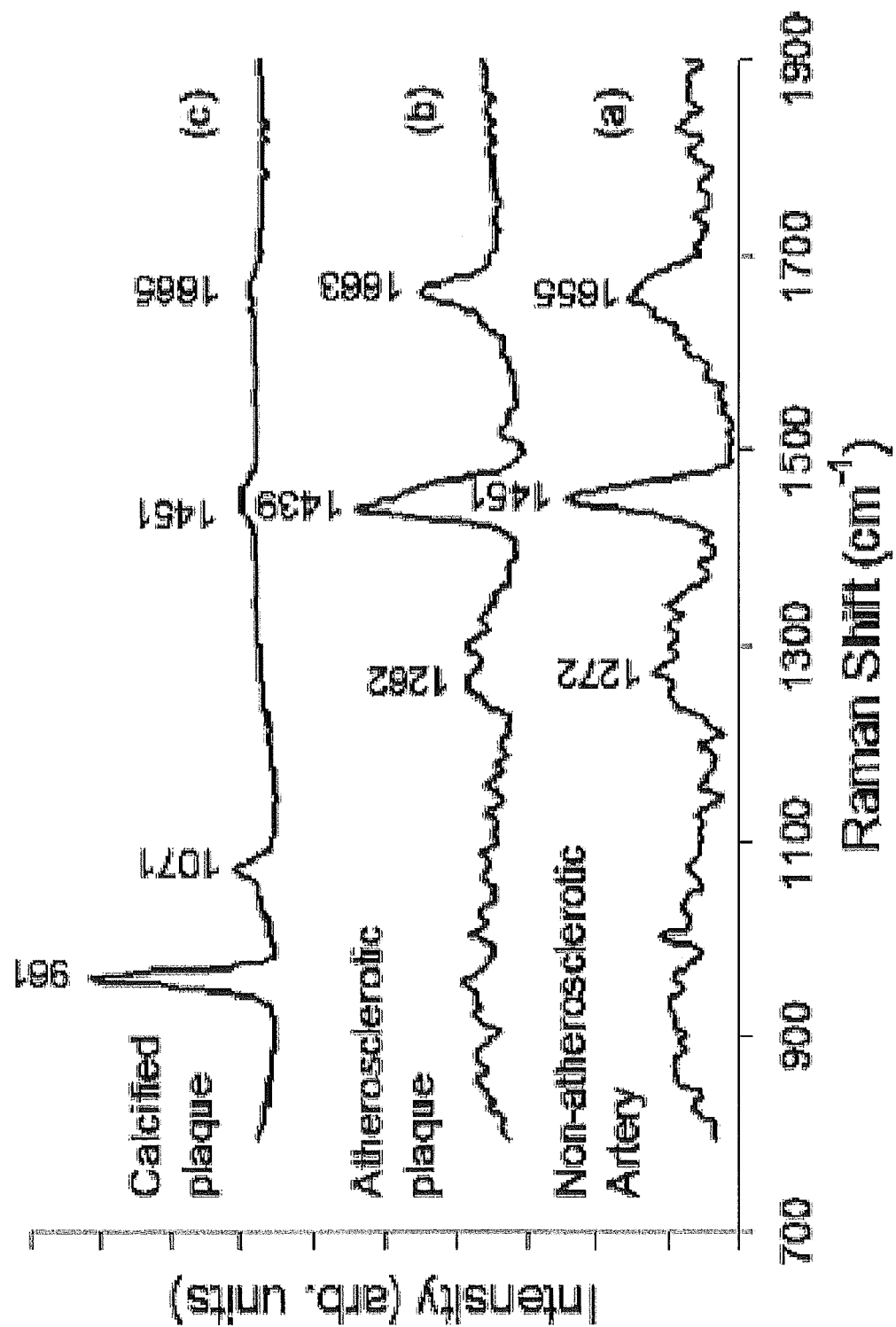
FIG. 7 shows Raman spectra of compounds identified in the human carotid artery.
Figure 8:
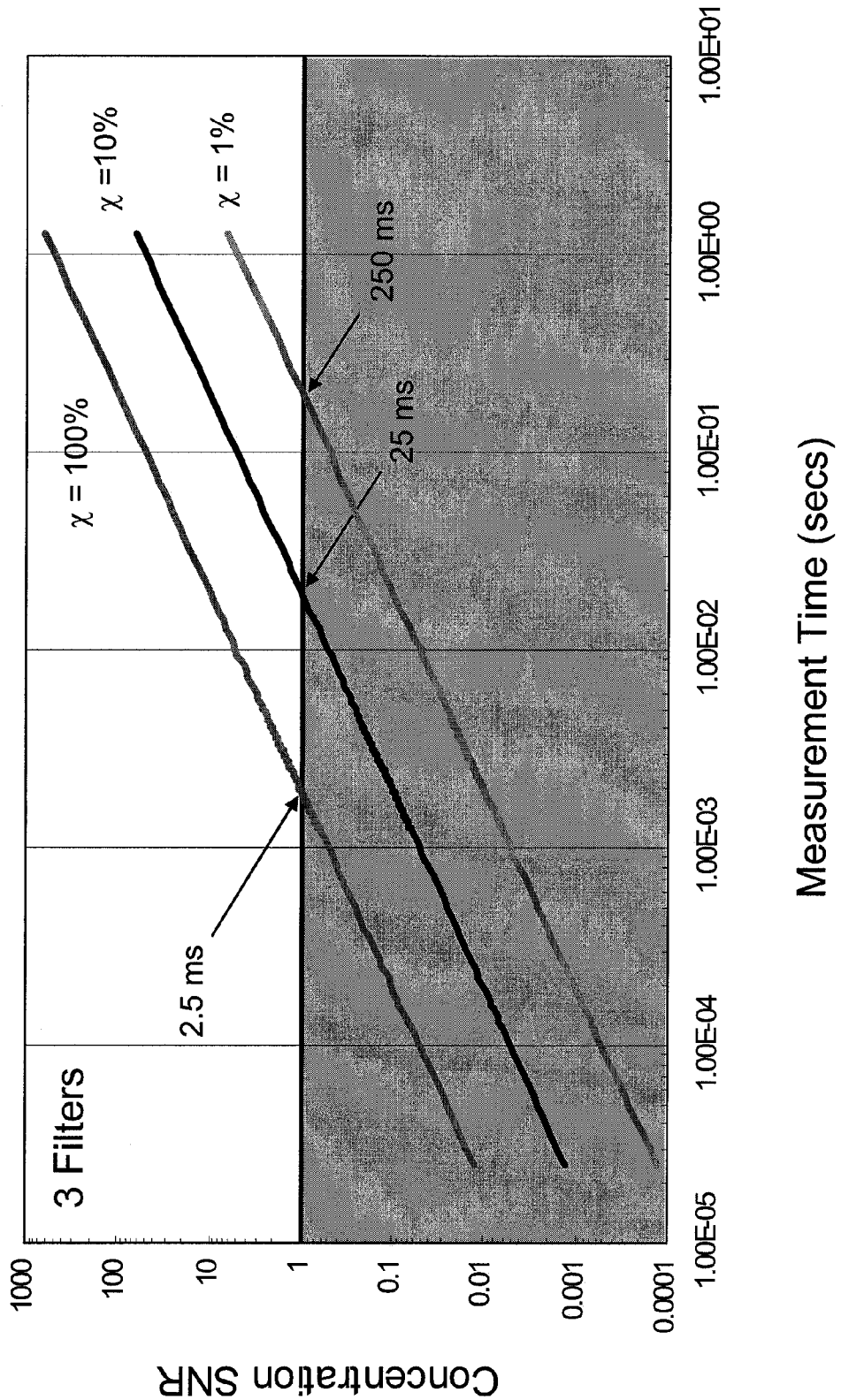
FIG. 8 shows the concentration signal to noise ratio as a function of measurement time for different concentrations of the compounds shown in FIG. 7.

As an illustration of the procedure mentioned FIG. 7 shows the characteristic Raman spectra for cholesterol, collagen and elastin. The result of using a set of filters for the specific task of measuring cholesterol, collagen and elastin is shown in FIG. 8. FIG. 8 displays different curves for the Signal-to-Noise ratio (SNR) of the concentration measurement, as a function of the measurement time of the Raman spectroscopy system. Clearly, for larger concentrations the SNR is higher, allowing for a faster measurement of the sample. As the concentrations are reduced, the SNR approaches the limiting value of 1, so longer measurement periods are needed in order to obtain a precise measurement.

Figure 9:
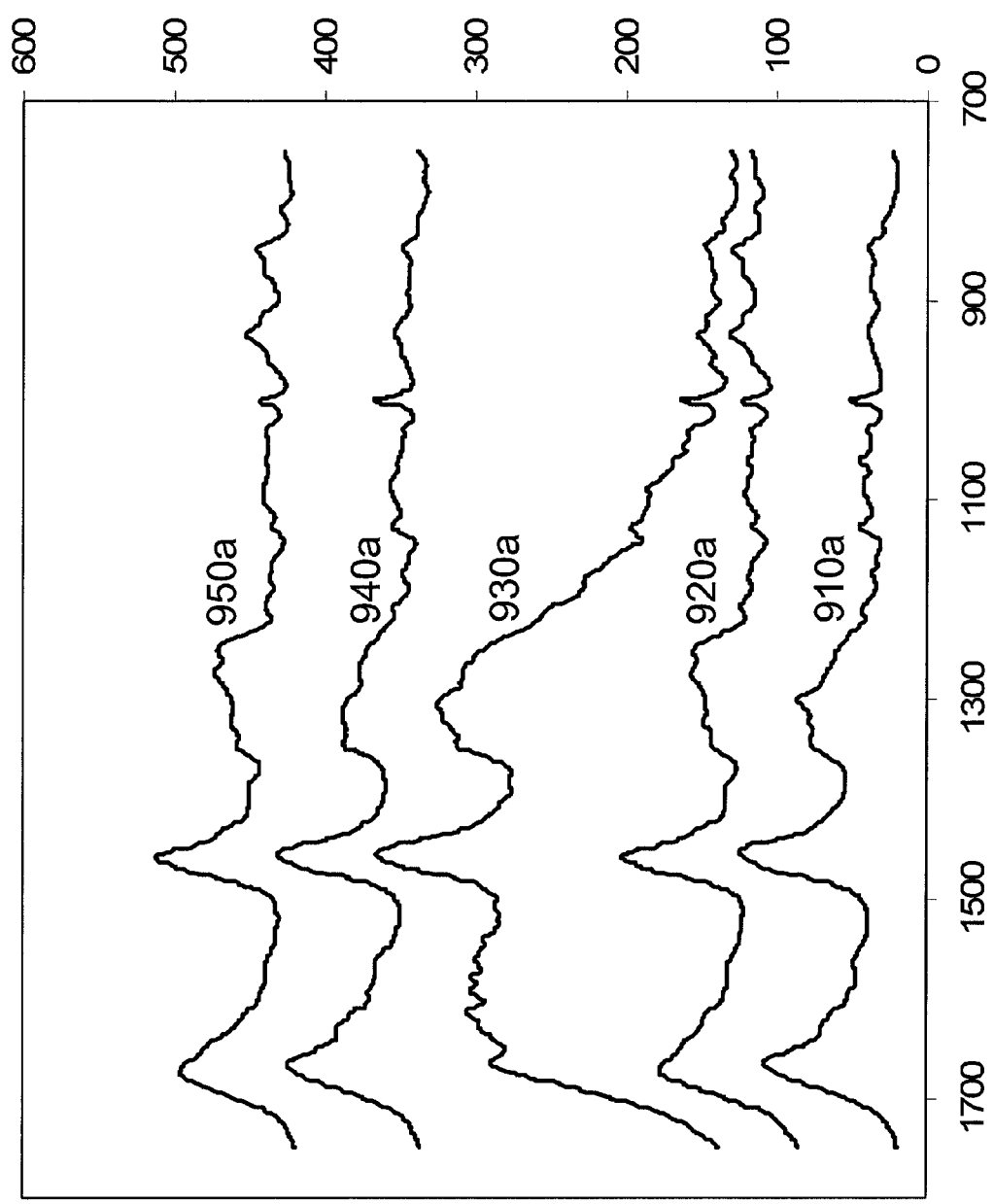
FIG. 9 shows Raman spectra from human skin tissue corresponding to five different clinical conditions.

FIG. 9 shows a sample Raman spectra of different skin tissue conditions. Data taken from Gniadecka et al. "Melanoma diagnosis by Raman Spectroscopy and Neural Networks: Structure Alterations in Proteins and Lipids in Intact Cancer Tissue," The Journal of Investigative Dermatology 122 443 (2004), incorporated herein by reference in its entirety. The spectra are averaged over 207 different individuals. FIG. 9 depicts spectra from normal tissue, 910a; basal cell carcinoma, 920a; Malignant Melanoma, 930a; pigmented nevi, 940a; and Seborrhoeic keratosis, 950a. The spectra of FIG. 9 are overlaid in sequence along the y-axis for ease of visualization, with the X-axis representing the Raman shift of the signal in units of $cm^{-1}$.

Figure 10:
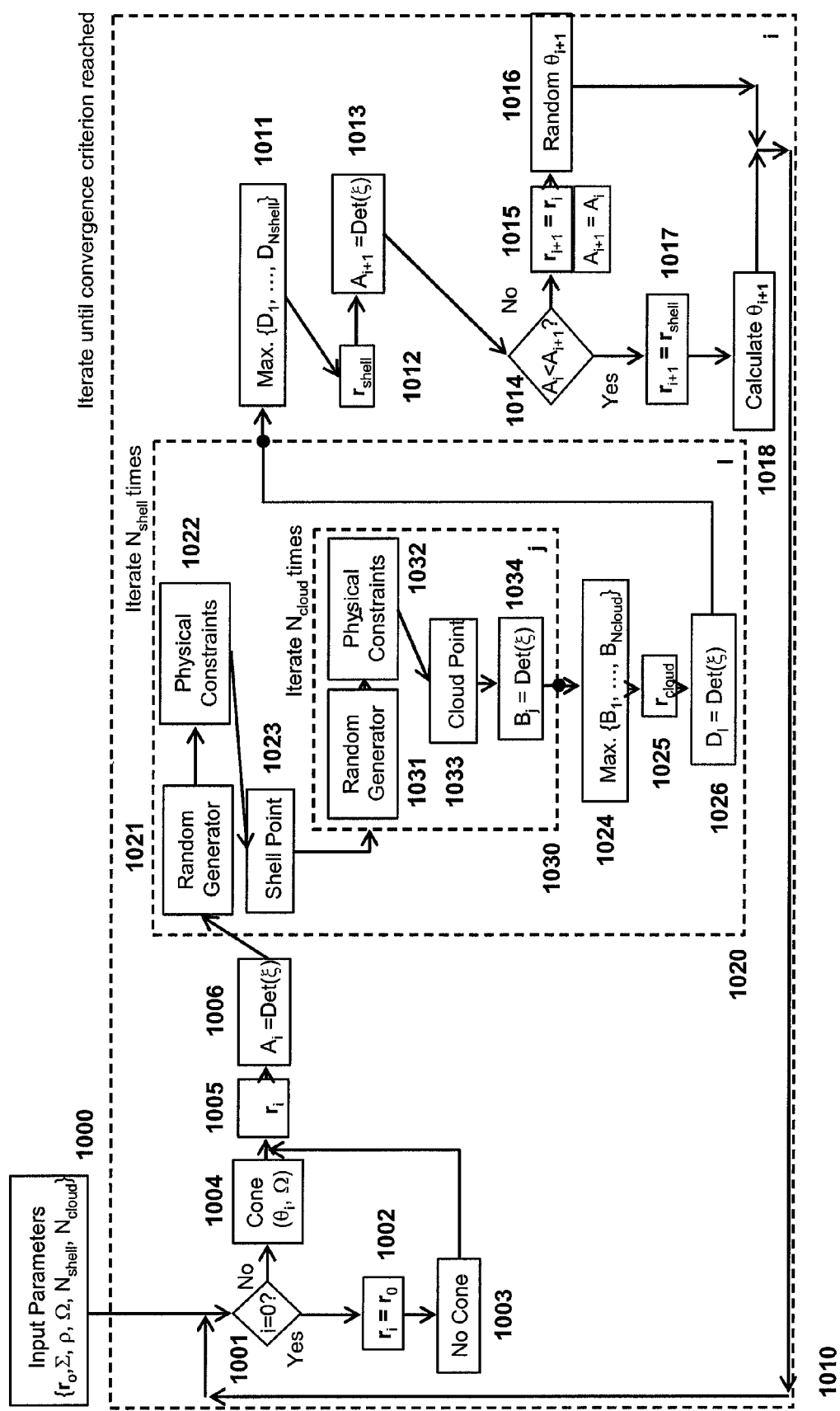
FIG. 10 shows a flow chart of a shell-cloud algorithm used to implement a dPCA measurement technique for diagnostics of skin pathological conditions using Raman spectroscopy system.

FIG. 10 shows a flow chart of the genetic algorithm used for optimization of the discriminating power of the dPCA technique, in terms of the parameters for the set of filters that will be utilized for measurement of a pathological skin condition. These parameters form a set of points, $\vec{r}_i$, in an L-dimensional space, $Q^L$, where L=f×n, 'f' is the number of parameters that characterize a single filter, and 'n' is the number of channels used in some embodiments of the Raman spectroscopy system disclosed herein. The data flow is quite general, independent of the spectroscopic technique used.

Furthermore, one of ordinary skill in the art of signal data processing and optimization programming would immediately realize that one embodiment of the data flow depicted in FIG. 10 may be applied for image-processing tasks. This is described in detail in co-pending U.S. patent application Ser. No. 11/767,458, which is incorporated herein by reference in its entirety.

Initial step 1000 consists of the choice of starting parameters: $\vec{r}_0$, starting point in $Q^L$; shell radius, $\Sigma$; cloud radius, $\rho$; angular tolerance $\Omega$; number of shell points, $N_{shell}$; and number of cloud points $N_{cloud}$. Starting point, $\vec{r}_0$, is selected. Sequence 1010 is started at step 1001, where if iteration parameter 'i' is zero, point $\vec{r}_i$ is selected as $\vec{r}_0$ at step 1002, and no cone of fixed angular width $\Omega$ is used to select the shell points at step 1003. If 'i' is different from zero, at step 1004 a value for $\theta_i$ is selected, together with $\Omega$. At step 1005 a value for $\vec{r}_i$ is selected, and at step 1006 a value $A_i$ is obtained from Det($\xi$) evaluated using point $\vec{r}_i$.

In sequence 1020, or "shell-scan", a number of points, $N_{shell}$, are randomly selected in step 1021, around an initial parameter point, $\vec{r}_i$, within a sphere of a fixed radius, $\Sigma$, centered at $\vec{r}_i$. This sphere will be herein referred to as a "shell." The "shell-points" are selected to satisfy a list of physical constraints provided in step 1022, and a normal distribution of directions around the center point, $\vec{r}_i$. This normal distribution has a fixed angular width $\Omega$ around a specific direction $\theta_i$. The direction $\theta_i$, is selected according to the angle formed between vectors $\vec{r}_i - \vec{r}_{i-1}$ and $\vec{r}_i$. The vector, $\vec{r}_{i-1}$ is the center of the "shell" used in a previous iteration of the routine. In step 1023 each of the shell points is selected, and second step 1030, called the "cloud-scan," is taken. In cloud scan 1030 a new set of $N_{cloud}$ points in $Q^L$ is selected, clustered around each of the shell points, within a sphere of fixed radius, $\rho$. This sphere will be herein referred to as a "cloud." In some embodiments of the procedure disclosed herein the radius of the cloud is selected to be smaller than the radius of the shell, and preferably much smaller. The points within a cloud are selected randomly in step 1031, but within the physical constraints provided in step 1032. In some embodiments of the present disclosure, cloud points are uniformly distributed around each of the shell points. In step 1033, a cloud point is selected, and in step 1034 the value of Det($\xi$) is evaluated. In step 1024, for each shell point, a point is selected within the corresponding cloud such that maximizes Det($\xi$). This point is labeled $\vec{r}_{cloud}$ in step 1025. In step 1026, the values of Det($\xi$) for all the $\vec{r}_{cloud}$ points in a shell are stored in a set. At step 1011, the point that maximizes Det($\xi$) in the set provided by step 1026 is selected, and labeled $\vec{r}_{shell}$ in step 1012.

The maximum value of Det($\xi$) in the set provided by step 1026 is stored in step 1013 and assigned a value $A_{i+1}$. Step 1014 queries whether or not the value provided by step 1013 ($A_{i+1}$) is larger than the value provided at the same stage in a prior iteration of the routine ($A_i$). If not, then point $\vec{r}_{i+1}$ is made equal to point $\vec{r}_i$, and $A_{i+1}$ is made equal to $A_i$, in step 1015. In step 1016 a random value for $\theta_{i+1}$ is selected for the next iteration of the routine. If the answer to the query in step 1014 is yes, then the point $\vec{r}_{i+1}$ is selected as $\vec{r}_{shell}$ in step 1017. At step 1018, the direction formed between vectors, $\vec{r}_{i+1} - \vec{r}_i$ and, $\vec{r}_i$, is selected as $\theta_{i+1}$. Once the value of $\theta_{i+1}$ is chosen, the steps from 1001 to 1018 can be repeated as described above for a number of times, P, until Det($\xi$) converges to a value that is substantially larger than any other possible value.

Figure 11:
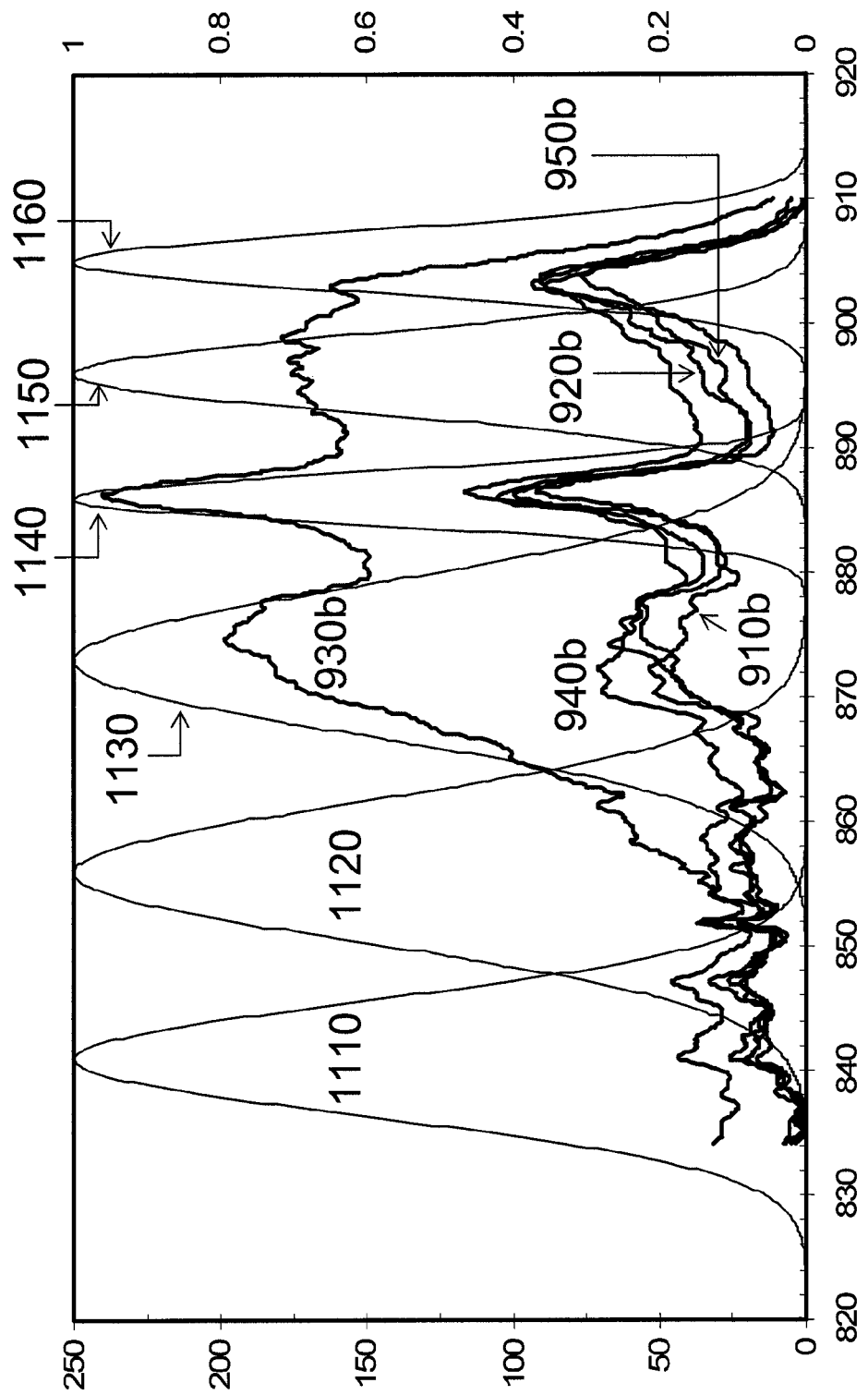
FIG. 11 shows the theoretical curves of the optical filters for diagnostics of skin pathological conditions obtained using the shell-cloud algorithm of FIG. 10.

FIG. 11 shows the result of the genetic algorithm described above, used for optimizing the discrimination power of the dPCA algorithm to be used in the RadiaLight® instrument. The model assumed a Gaussian profile for all the filters. The number of parameters used to characterize each channel was f=3, corresponding to: center wavelength of the filter, bandwidth of the filter, and relative amplitude of the signal used for each channel (in absolute numbers from 0 to 1). In the embodiment depicted in FIG. 11, six (6) filters have been selected to cover the different classes of skin tissue, according to the embodiments of FIG. 10. Therefore, a parameter space having L=3×6=18 dimensions was used in the genetic algorithm. The resulting filters 1110-1160 are overlaid to the Raman spectra of the tissues in question, namely normal tissue, 910b; basal cell carcinoma, 920b; Malignant Melanoma, 930b; pigmented nevi, 940b; and Seborrhoeic keratosis, 950b. In the embodiment shown in FIG. 11, the X-axis corresponds to wavelength (nm), and is obtained in relation to a pump laser with a wavelength of 785 nm.

Table I shows a list of the properties of the six optical band-pass filters determined with the genetic algorithm as described above, together with a list of the measured properties of the actual filters used in one embodiment of the Raman spectroscopy system described herein. In this embodiment, the optical filters were provided by Omega Optical, Inc. of Brattleboro, Vt. Two extra optical filters were added to the instrument due to the availability of the optical channels.

TABLE I

| Genetic Algorithm/Filters used (Omega Optical, Inc.) | |
| --- | --- |
| Center Wavelength (nm) | Bandwidth (nm) |
| 841.0/840.7 | 13.0/13.5 |
| NA/850.0 | NA/5.0 |
| 856.0/853.0 | 16.0/18.3 |
| 873.0/874.9 | 17.0/14.1 |
| 886.0/887.0 | 6.0/9.9 |
| 896.0/899.6 | 9.0/10.0 |
| 905.0/903.7 | 7.0/8.9 |
| NA/911.0 | NA/6.0 |

Figure 12:
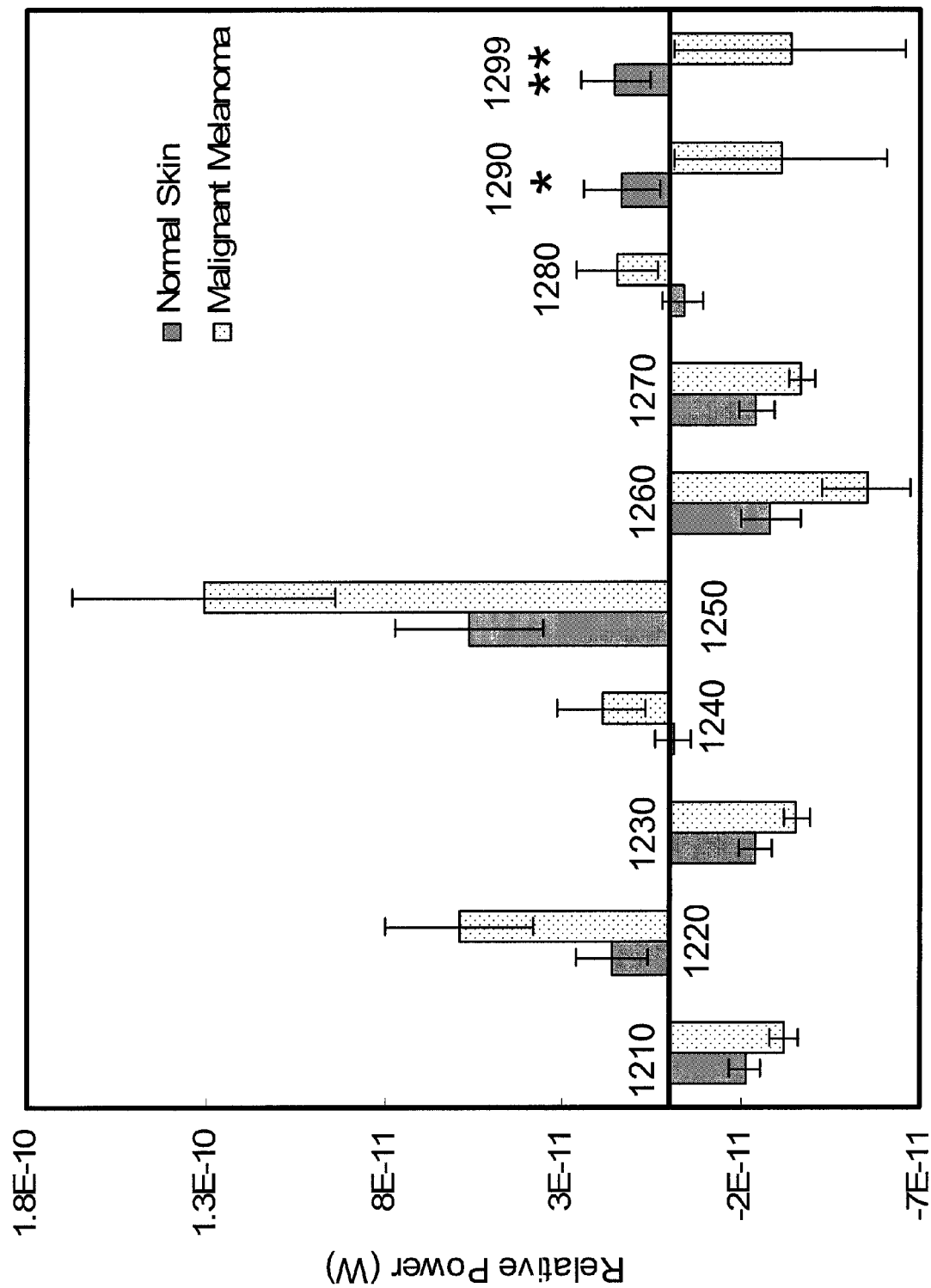
FIG. 12 shows the results of a measurement of normal skin and malignant melanoma samples, obtained according to one embodiment of the present disclosure.

FIG. 12 shows statistical analysis of the results from measurements performed in tissue samples provided by Biomax, Inc. of Rockville, Md. The test array of human skin biopsies provided corresponds to part no. ME207. This array includes a microscope slide with the 207 cores of paraffin embedded human skin tissue in place. Each core is ~2 mm in diam. Since the measurements are taken relative to the mean of the 8 channel values for each spectra, some of the channels show a "negative" projection as the Normal->Malignant progression takes place. In the embodiment of the measurement instrument and technique depicted in FIG. 12, the largest signal corresponds to the overall collected Raman signal across a spectral range from approximately 820 nm to approximately 920 nm, without any filtering therein, other than the filtering out of the Rayleigh scattered signal. Each of the measurements depicted in FIG. 12 is labeled as follows: channel 1210, filter at 874.9 nm; channel 1220, filter at 850 nm; channel 1230, filter at 911 nm; channel 1240, filter at 840.7 nm; channel 1250, total Raman signal across a spectral range from approximately 820 nm to approximately 920 nm; channel 1260, filter at 903.7 nm; channel 1270, filter at 899.6 nm; channel 1280, filter at 887 nm; channel 1290, marked with an asterisk * since it corresponds to a different measurement class, namely the laser current (in arbitrary units) used to perform the measurement; and channel 1299, marked with a double asterisk  since it corresponds to a different measurement class, namely the Rayleigh signal obtained from core sample (in arbitrary units). The error bars displayed in the data depicted in FIG. 12, obtained according to one embodiment of the present disclosure, correspond to the standard deviation of the measurements obtained for the sample set used. From the results shown in FIG. 12**, it is clear that the transition between normal skin tissue and tissue affected with malignant melanoma can be established within the statistical error of the measurements performed.

Note that the values associated with a given channel for the purpose of a dPCA analysis as described in co-pending U.S. patent application Ser. No. 11/767,458, which is incorporated herein by reference in its entirety, need not be all power values associated with a specific portion of the Raman emission spectrum of the tissue. Channel 1290 and 1299 in FIG. 12, for example, illustrate embodiments of channel values associated with the value of an electric current used to drive the pump laser (1290), or the value of the Rayleigh signal obtained from the tissue (1299). In general, one of ordinary skill in the art would recognize that the values used to enter as part of the loadings vector in a dPCA analysis technique may be associated with any other controllable parameter that describes the configuration of a given measurement and upon which a linear dependence of the measured signal may be expected. For example, in the case of the value of the current used to drive the pump laser, it may be reasoned that: it is a controllable, repeatable and measurable value, and within a range of values it is linearly related to the optical power delivered by the pump laser onto the sample. Therefore the value of the current used to drive the pump laser has a linear relation to the Raman signal eventually measured by the photo-detector. Likewise, in the case of the Rayleigh scattered signal, this may be associated with a certain absorption coefficient of the skin tissue, and a certain penetration depth, which have an impact in the magnitude of the Raman signal collected and measured by the system.

Figure 13:
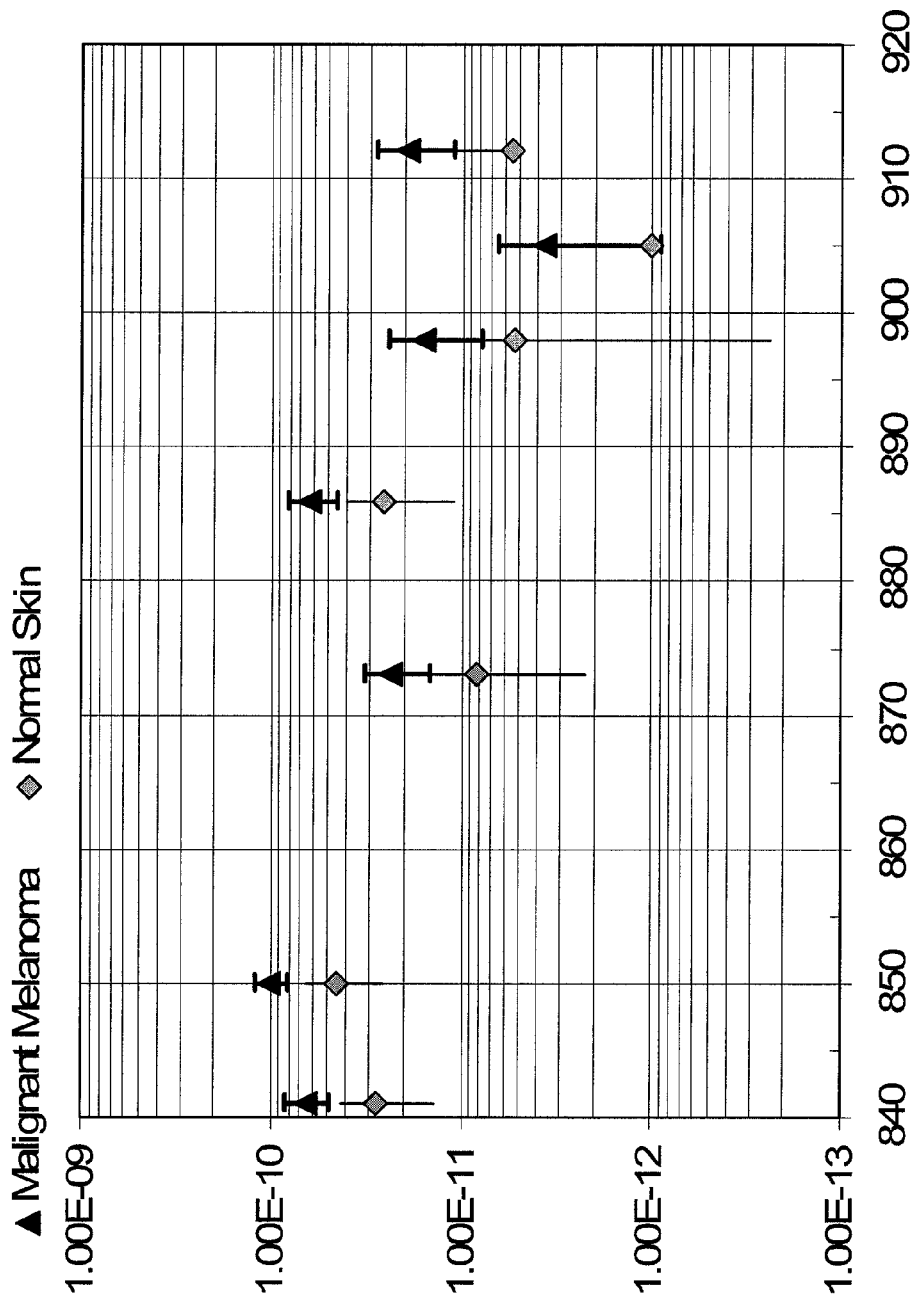
FIG. 13 shows spectral results of a measurement of normal skin and malignant melanoma samples, obtained according to one embodiment of the present disclosure.

FIG. 13 shows measurements performed on the samples provided by ME207 from Biomax. In this case, only two classes are used for discrimination: malignant melanoma/ normal tissue. Error bars represent averages over 5×20 measurements performed for a particular class on each one of the filter channels. The plot of FIG. 13 consists of one embodiment of the present disclosure wherein a band-pass filter is associated with any given channel, and photons corresponding to the Raman spectrum of the sample are collected. Thus, the center wavelength of the filter in question is plotted along the X-axis of FIG. 13, whereas the averaged power measured with the photo-detector when the unit is aligned with respect to said optical channel, is plotted along the Y-axis of FIG. 13.

Figure 14:
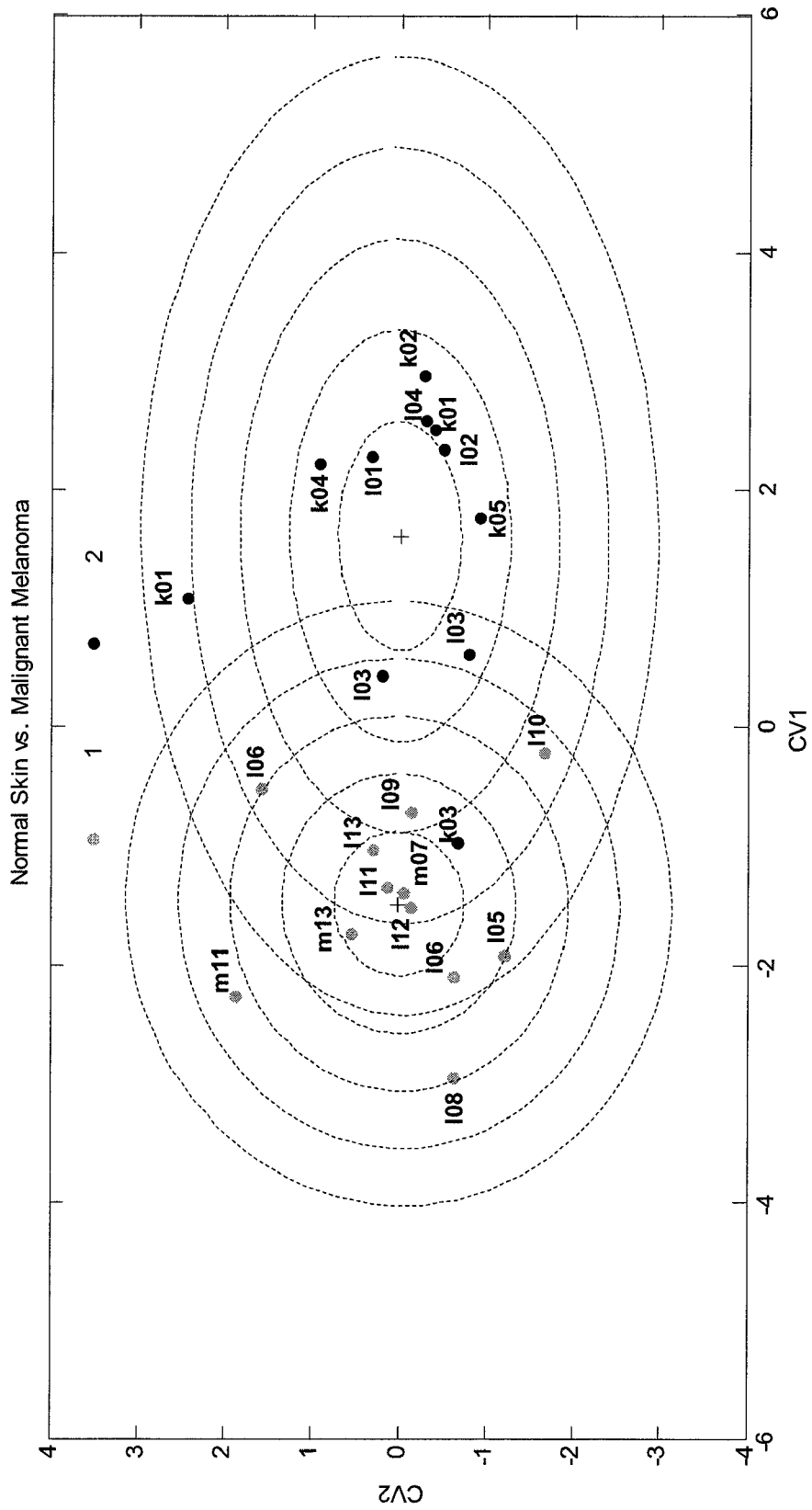
FIG. 14 shows a canonical variables result of a measurement of normal skin and malignant melanoma samples, obtained according to one embodiment of the present disclosure.

FIG. 14 shows a canonical-variables analysis of the results from the Biomax, ME207 samples provided. The canonical analysis depicted in FIG. 14 was obtained by using the data presented in FIGS. 12 and 13, and a MANOVA I software package contained in a MATLAB application. One of regular skill in the art would realize that a canonical variables analysis such as the one shown in FIG. 14 can be implemented in a variety of ways, using multiple commercially available software packages. In this case, the Raman signal clearly offers efficient discrimination ability for a binary classification scheme (normal tissue vs. malignant melanoma). The data points, which are clearly distinguishable between two groups, are as follows: malignant melanoma→{k01, k03, k04, k05, I01, I02, I03}; normal tissue→{I05, I06, I08, I09, I10, I11, I12, I13, m07, m11, m13}. The only overlapping data point corresponds to sample k03, which is malignant melanoma tissue, indistinguishable from normal skin tissue, according to the embodiment of the present disclosure depicted in FIG. 14.

Figure 15:
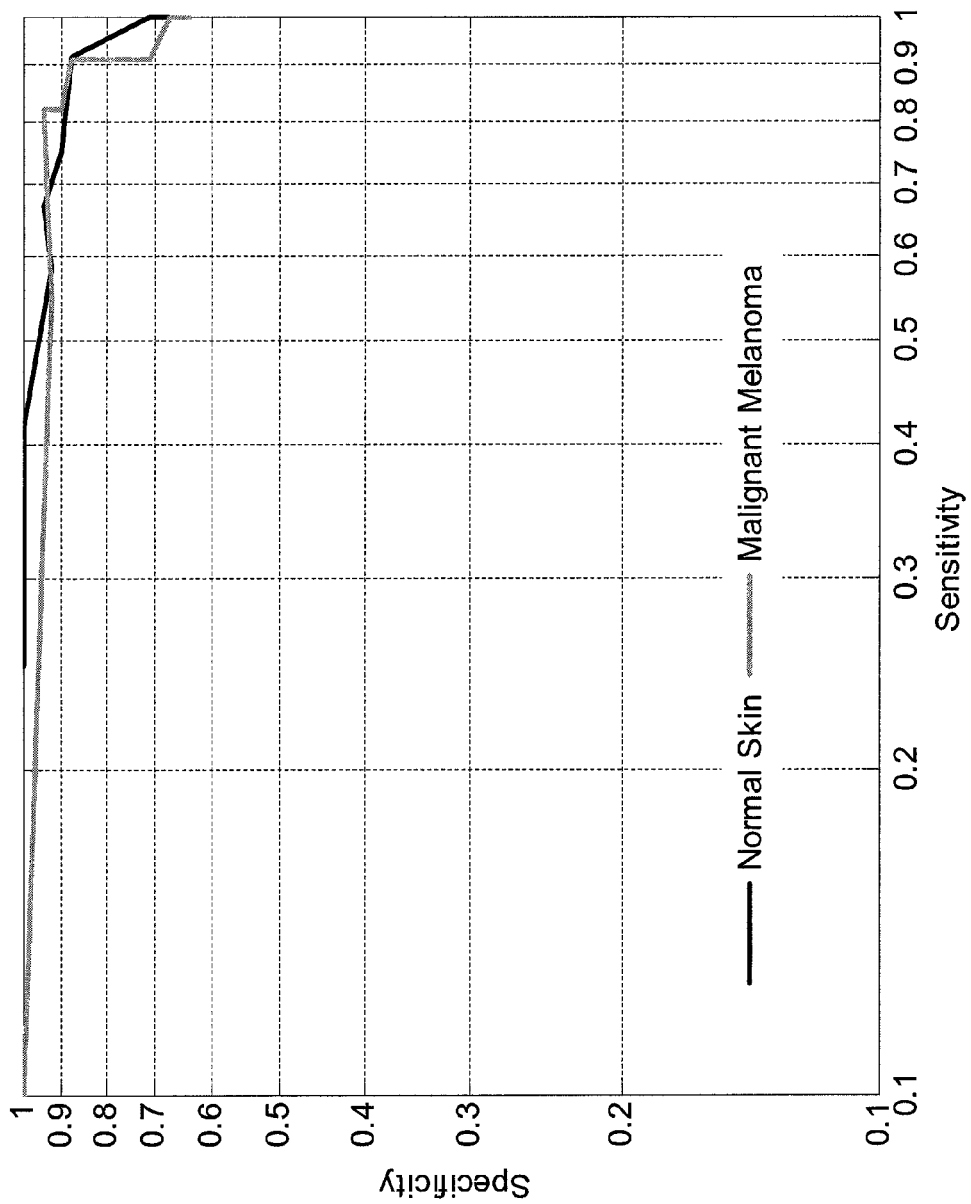
FIG. 15 shows a receiver operating characteristic curve (ROC) for a measurement of normal skin and malignant melanoma samples, obtained according to one embodiment of the present disclosure.

FIG. 15 shows a receiver operating characteristic (ROC) curve obtained for the data from Biomax, ME 207 sample. An ROC curve is a plot of specificity vs. sensitivity for a binary classifier system. In some embodiments of the present disclosure, such as the one described in FIG. 15, the binary classification corresponds to normal skin vs. malignant melanoma condition of the skin tissue sample. The maximum specificity×sensitivity point is obtained at the 90% level for each of the binary conditions. This would be the quality of the system as is, which about 10-15% better than current dermatology experts.

Figure 16:
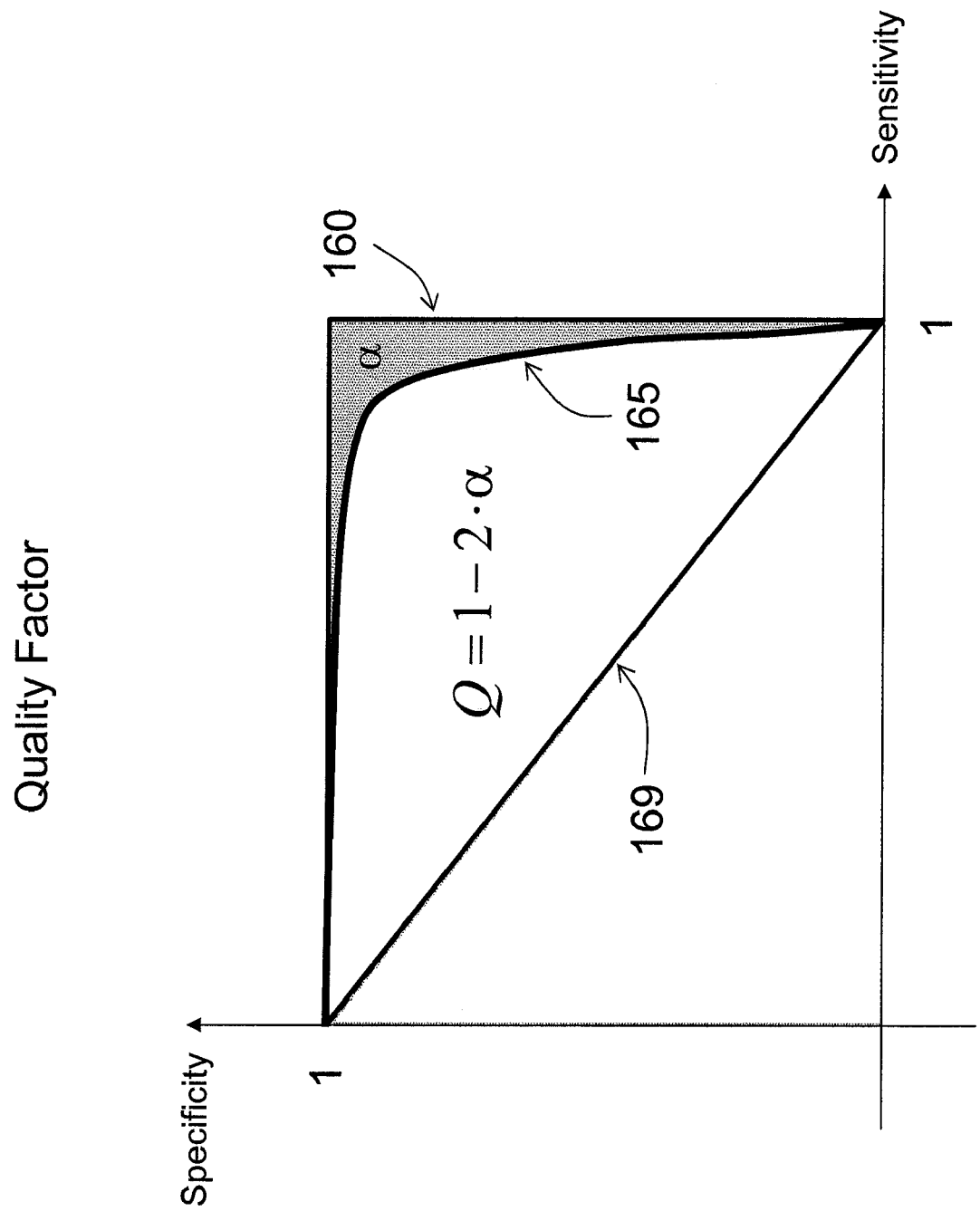
FIG. 16 shows how a value for a quality factor can be obtained from an ROC curve for a given instrument, according to some embodiments of the present disclosure.

FIG. 16 shows a schematic representation of a variable defined as "quality" factor, Q, corresponding to a clinical diagnostics instrument. This variable is useful to determine design goals and specifications. In some embodiments of the present disclosure, quality factor, Q, represents the proportion of the area, α, between true ROC curve 165 and ideal ROC curve 160. In some embodiments of the present disclosure, quality factor, Q, is related to area, by the following equation:

$$Q = 1 - 2 \cdot \alpha \quad (8)$$

In FIG. 16, ideal ROC curve 160 has a constant value of specificity equal to 1, for values of sensitivity from 0 to 1. Thus, a quality factor, Q, equal to 1, corresponds to the ideal detection mechanism. On the other hand, the lowest value that the quality factor may have is Q=0, corresponding to a detection mechanism that is purely random. Such a detection mechanism will have random curve 169 as its ROC characteristic.

Figure 17:
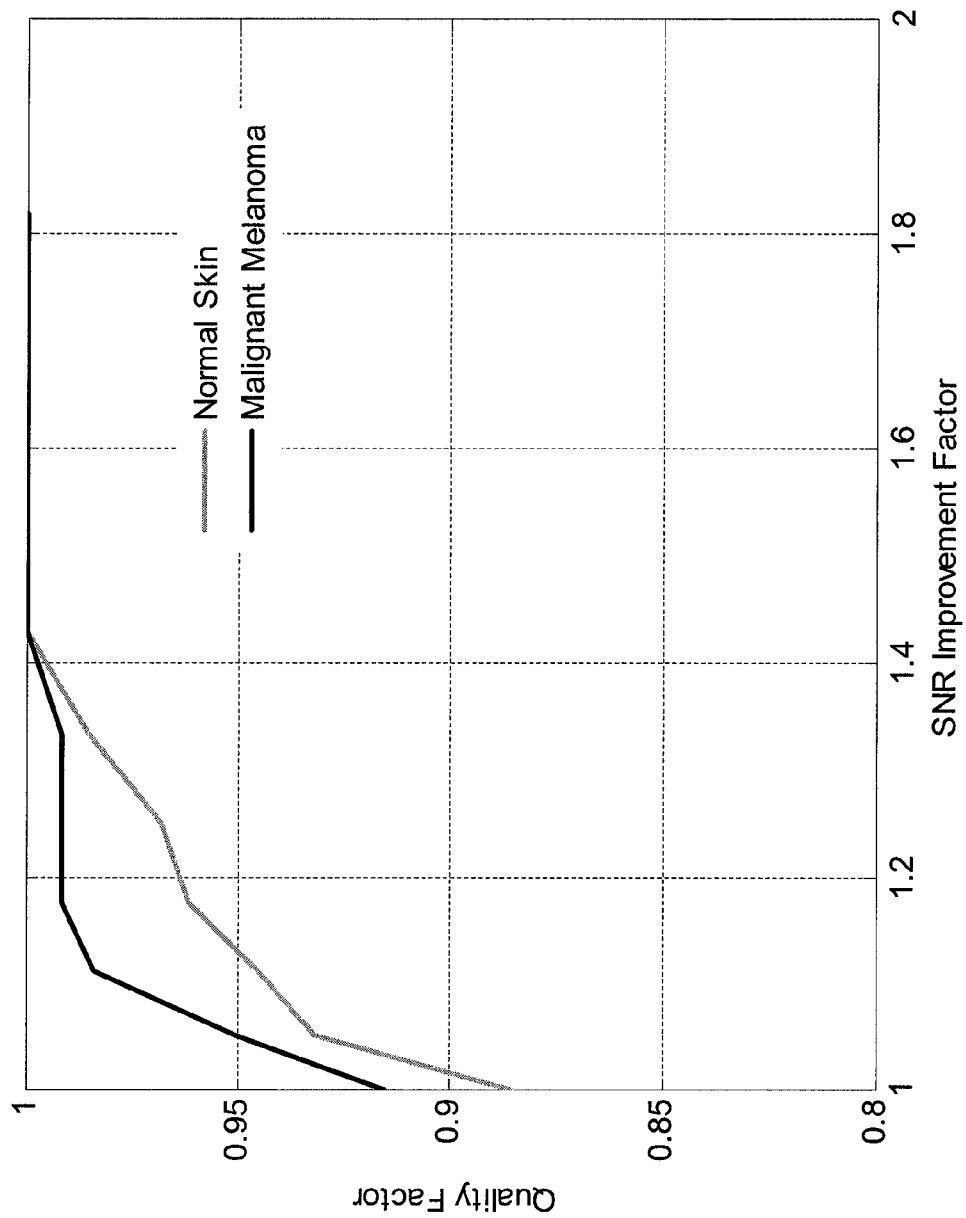
FIG. 17 shows the quality factor as a function of the SNR improvement factor for the Raman spectroscopy system according to some embodiments of the present disclosure.

FIG. 17 shows a quality improvement chart for one embodiment of the present disclosure as tested on the Biomax ME 207 array. Current performance at the 89-92% level can be improved to a 98% level for both classes by increasing the SNR level by 40%.

Figure 18:
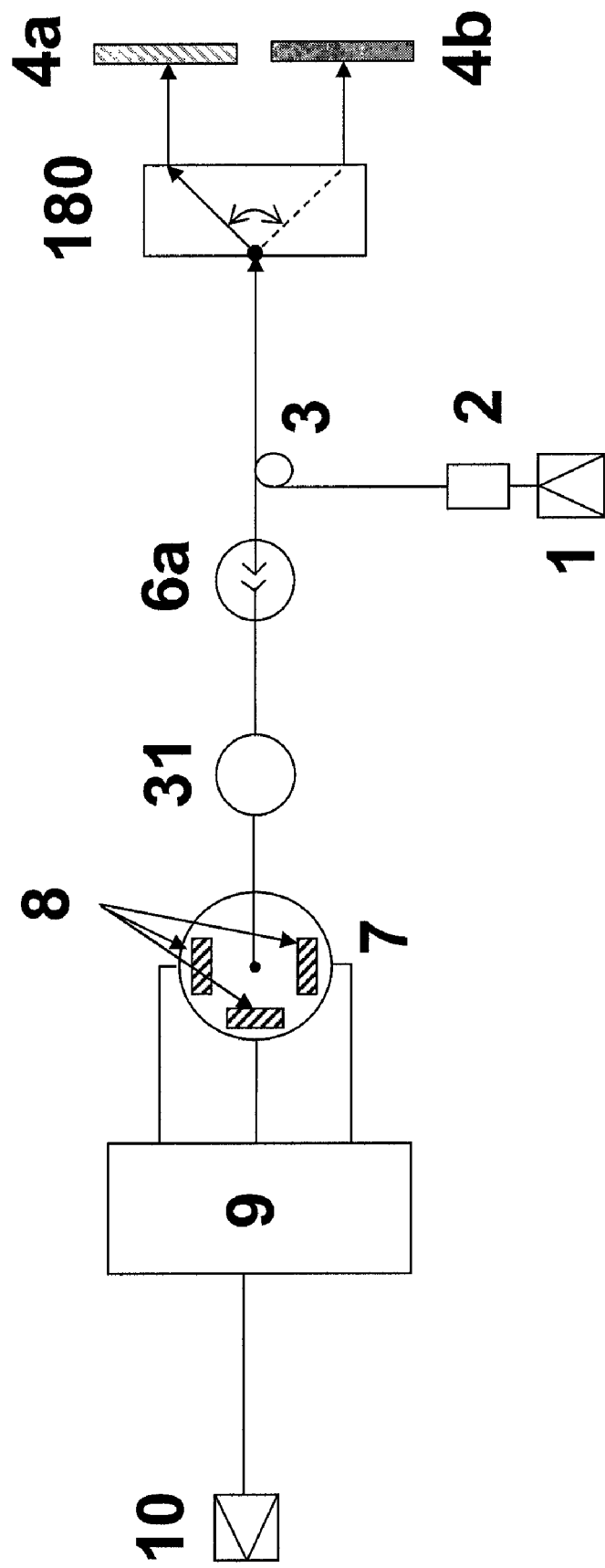
FIG. 18 shows a Raman spectroscopy system for the diagnostics of pathological skin conditions using a reference arm and a sampling arm, according to some embodiments of the present disclosure.

FIG. 18 shows the use of a time-resolved Raman spectrometer for the diagnostics of skin pathological conditions according to some embodiments of the present disclosure. Elements in FIG. 18 that have been previously described have been assigned the same reference numerals as in previous figures (cf. FIG. 1-3), and their description will not be repeated hereafter. In FIG. 18, switch 180 is used to divert the optical head of the time-resolved Raman spectrometer from a first area of the skin 4a to a second area of the skin 4b. First area of skin 4a may correspond to a portion of the tissue that is clearly under normal conditions, as a person of ordinary skill may determine, e.g. a general medicine practitioner, doctor, or nurse. Second area of the skin 4b may correspond to an area where determination of the tissue condition may be more difficult, or may be less clear or less obvious for one of ordinary skill, or even an expert dermatologist. By performing the two alternate measurements on first and second areas of the skin, 4a and 4b, a first baseline determination may be made based on the normal skin measurement. With these values, the indeterminate portion of the tissue in the second measurement may be directly compared to the normal tissue.

The above description is illustrative only. Those skilled in the art will recognize other embodiments of the invention which can be implemented in view of this disclosure. As technology advances, other embodiments of this invention will be capable of being implemented. The claims are intended to cover all these possible embodiments.

What is claimed is:

1. A Raman spectroscopy system comprising:
    a plurality of light transmission channels;
    a time-division multiplexing device for distributing, in a time multiplexed manner, at least one portion of Raman Stokes radiation scattered from a biological tissue sample to each of the plurality of light transmission channels, wherein the Raman Stokes radiation is formed as a result of light impinging on the biological tissue sample;
    a light detector for detecting the distributed portion of the Raman Stokes radiation passed by each of said transmission channels, further wherein each of the transmission channels comprises a filter to select a specific wavelength range for each channel;
    an analyzing processor for processing a signal from the light detector to detect at least one particular condition of the biological tissue sample.

2. The system of claim 1, further comprising: a synchronizing circuit for turning on the light detector only when the distributed at least one portion of the Raman Stokes radiation from the time-division multiplexing device is expected at the light detector and otherwise leaving off the light detector.

3. A Raman spectroscopy system comprising:
    a plurality of light sources, wherein each light source produces at least one continuous-wave first signal to be directed at a biological tissue sample;
    a time division multiplexing device for transmitting, in a time multiplexed manner, the at least one continuous-wave first signal from each light source to the biological tissue sample wherein Raman Stokes radiation is scattered as a result of the at least one continuous-wave first signal impinging on the biological tissue sample;
    a detector responsive to at least one portion of the scattered Raman Stokes radiation for producing a second signal representing at least one particular condition of the biological tissue sample; and
    a synchronizing circuit for turning on the detector at the times that the scattered Raman Stokes radiation is expected at the detector.

4. The system as in claim 3 further comprising: a light transmission channel for transmitting the at least one portion of the Raman Stokes radiation scattered from the biological tissue sample to the detector; and a narrow pass-band filter in series with the light transmission channel to pass the at least one portion of the Raman Stokes radiation scattered from the biological tissue sample.

5. The system of claim 3 further comprising: an analyzing processor connected to the detector for processing each second signal from the detector to detect the at least one particular condition of the biological tissue sample.

6. The system of claim 3 wherein the synchronizing circuit synchronizes the turning on of the detector with the arrival at the detector of the at least one portion of the Raman Stokes radiation scattered from the biological tissue sample.

7. The system of claim 3 wherein the synchronizing circuit synchronizes the turning on of the detector with the arrival at the detector of the at least one portion of the Raman Stokes radiation scattered from the biological tissue sample so as to maximize a sensitivity of the system.

8. The system of claim 5 wherein the synchronizing circuit synchronizes the turning on of the detector with the arrival at the detector of the at least one portion of the Raman Stokes radiation scattered from the biological tissue sample so as to reduce a dark count and noise level present at the analyzing processor.

9. The system as in claim 3 wherein the plurality of light sources comprise a plurality of lasers, each laser operating at a different wavelength from the other lasers.

10. The system as in claim 3 wherein the plurality of light sources comprise emission lamps.

11. The system as in claim 10 further comprising: a plurality of narrow band-pass filters arranged to allow only a portion of the light from each emission lamp to reach the biological tissue sample.

12. The system of claim 10 wherein each emission lamp comprises a lamp containing mercury, xenon, neon or other suitable gas capable of emitting the light.

13. A method of implementing a Raman spectroscopy procedure which comprises:
    causing a light to impinge on a biological tissue sample thereby to scatter the light from said sample to produce Raman Stokes radiation;
    distributing, in a time sequence manner, at least one portion of the Raman Stokes radiation to each of a plurality of transmission channels so as to cause the at least one portion of the Raman Stokes radiation transmitted by each transmission channels to arrive in a pre-determined time sequence at an optical detector;
    synchronizing a process of turning on of the optical detector with the arrival, in the pre-determined sequence, at the optical detector of the at least one portion of the Raman Stokes radiation from each transmission channel; and
    analyzing at least one signal from the optical detector to determine at least one particular condition of the biological tissue sample.

14. The method of claim 13, wherein the analyzing step further comprises using a discrete principle component analysis procedure to detect the at least one particular condition of the biological tissue sample, wherein the at least one particular condition is presence of an analyte.

15. The method of claim 14 wherein the at least one particular condition is presence of two or more discrete analytes.

16. The method of claim 13 wherein the distributing step further comprises using a time-division multiplexing device to distribute, in the time sequence manner, the at least one portion of the Raman Stokes radiation to each of a plurality of transmission channels such that two or more particular conditions of the biological tissue sample can be detected in one cycle of rotation of the time-division multiplexing device.

17. A method of implementing Raman spectroscopy comprising:
    producing, from each of a plurality of light sources, at least one continuous-wave first signal to be directed at a biological tissue sample;
    transmitting, in a time sequence manner, the at least one continuous-wave first signal from each light source the biological tissue sample, wherein Raman Stokes radiation is scattered as a result of the at least one continuous-wave first signal impinging on the biological tissue sample;
    transmitting at least one portion of the Raman Stokes radiation scattered from the biological tissue sample to a detector;
    producing at least one second signal at the detector representing at least one particular condition of the biological tissue sample; and
    synchronizing a process of turning on of the detector with the arrival at the detector of the at least one portion of the Raman Stokes radiation scattered from the biological tissue sample.

18. The system of claim 1, wherein the at least one particular condition is melanoma.

19. The system of claim 3, wherein the at least one particular condition is melanoma.

20. The system of claim 5, wherein the at least one particular condition is melanoma.

21. The method of claim 13, wherein the at least one particular condition is melanoma.

22. The method of claim 17, further comprising a step of analyzing the at least one second signal from the optical detector to determine at least one particular condition of the biological tissue sample.

23. The method of claim 22, wherein the at least one particular condition is melanoma.

24. The method of claim 22, wherein the analyzing step further comprises using a discrete principle component analysis procedure to detect the at least one particular condition of the biological tissue sample, wherein the at least one particular condition is presence of an analyte.

25. The method of claim 24 wherein the at least one particular condition is presence of two or more discrete analytes.

26. The method of claim 17 wherein the transmitting step further comprises using a time-division multiplexing device to transmit, in the time multiplexed manner, the at least one continuous-wave first signal from each light source the biological tissue sample.

* * * * *